(12) United States Patent
Ito et al.

(10) Patent No.: US 10,429,403 B2
(45) Date of Patent: Oct. 1, 2019

(54) HEAD DEVICE FOR MOUNTING DISPENSING TIP THEREON, AND MOVEMENT DEVICE USING SAME

(71) Applicant: YAMAHA HATSUDOKI KABUSHIKI KAISHA, Iwata-shi, Shizuoka-ken (JP)

(72) Inventors: Saburo Ito, Shizuoka (JP); Yukimasa Osada, Shizuoka (JP); Yohei Izume, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 42 days.

(21) Appl. No.: 15/318,929

(22) PCT Filed: Jun. 17, 2014

(86) PCT No.: PCT/JP2014/065970
§ 371 (c)(1),
(2) Date: Dec. 14, 2016

(87) PCT Pub. No.: WO2015/193958
PCT Pub. Date: Dec. 23, 2015

(65) Prior Publication Data
US 2017/0131315 A1    May 11, 2017

(51) Int. Cl.
*G01N 35/10* (2006.01)
*G01N 1/14* (2006.01)
*B01L 3/02* (2006.01)

(52) U.S. Cl.
CPC ............ *G01N 35/1011* (2013.01); *B01L 3/02* (2013.01); *B01L 3/0227* (2013.01); *B01L 3/0231* (2013.01);
(Continued)

(58) Field of Classification Search
CPC combination set(s) only.
See application file for complete search history.

(56) References Cited

U.S. PATENT DOCUMENTS

| | | |
|---|---|---|
| 4,586,546 A | 5/1986 | Mezei et al. |
| 4,844,298 A | 7/1989 | Ohoka et al. |

(Continued)

FOREIGN PATENT DOCUMENTS

| | | |
|---|---|---|
| CN | 102135084 A | 7/2011 |
| CN | 103691498 A | 4/2014 |

(Continued)

OTHER PUBLICATIONS

The extended European search report issued by the European Patent Office dated Jun. 13, 2017, which corresponds to European Patent Application No. 14895175.9-1371 and is related to U.S. Appl. No. 15/318,929.

(Continued)

*Primary Examiner* — Brian R Gordon
(74) *Attorney, Agent, or Firm* — Studebaker & Brackett PC

(57) ABSTRACT

A head device for mounting a dispensing tip includes a piston member, a first shaft member to move the piston member in an up-down direction, a tubular rod including a tubular space having a cylinder space in which the piston member is housed to move in the up-down direction and including a tip mounting portion into which a base end portion of the dispensing tip is fitted, a first frame equipped with the first shaft member and the tubular rod, a second shaft member engaging with the first frame to move the first frame, a second frame equipped with the second shaft member and including a guide portion configured to guide movement of the tubular rod in the up-down direction in association with the movement of the first frame in the (Continued)

up-down direction, and a shaft controller configured to control operation of the first and second shaft members.

9 Claims, 17 Drawing Sheets

(52) U.S. Cl.
 CPC .............. *B01L 3/0279* (2013.01); *G01N 1/14* (2013.01); *B01L 2200/026* (2013.01); *B01L 2400/0478* (2013.01); *B01L 2400/082* (2013.01); *G01N 35/1081* (2013.01); *G01N 2035/103* (2013.01)

(56) References Cited

U.S. PATENT DOCUMENTS

| | | | |
|---|---|---|---|
| 5,111,703 A | 5/1992 | Allen | |
| 5,192,511 A | 3/1993 | Roach | |
| 2003/0049170 A1* | 3/2003 | Tamura | B01L 3/0275 422/63 |
| 2003/0159525 A1 | 8/2003 | Viot | |
| 2003/0190263 A1 | 10/2003 | Yiu | |
| 2004/0067170 A1* | 4/2004 | Higuchi | B01L 3/0279 422/511 |
| 2004/0096360 A1* | 5/2004 | Toi | G01N 35/1067 422/63 |
| 2004/0122222 A1 | 6/2004 | Sakurai et al. | |
| 2004/0159675 A1 | 8/2004 | Nishino | |
| 2005/0191215 A1 | 9/2005 | Viot | |
| 2009/0114574 A1* | 5/2009 | Deggerdal | B01L 3/0279 209/214 |
| 2010/0043575 A1 | 2/2010 | Tajima | |
| 2010/0236324 A1 | 9/2010 | Tajima et al. | |
| 2011/0015381 A1 | 1/2011 | Sakurai et al. | |
| 2011/0132110 A1 | 6/2011 | Kimura et al. | |
| 2011/0182781 A1 | 7/2011 | Dzuong | |
| 2011/0182782 A1 | 7/2011 | Dzuong | |
| 2013/0084606 A1* | 4/2013 | Sugimoto | B01L 7/52 435/91.2 |
| 2013/0130369 A1* | 5/2013 | Wilson | G16B 99/00 435/289.1 |
| 2014/0234949 A1* | 8/2014 | Wasson | G01N 35/1065 435/287.2 |
| 2016/0023203 A1* | 1/2016 | Richardson | B01L 3/0279 422/511 |
| 2016/0320381 A1* | 11/2016 | Holmes | B01L 3/0217 |
| 2017/0003310 A1* | 1/2017 | Shohmi | G01N 35/1065 |
| 2017/0361315 A1* | 12/2017 | Guzman | B01L 3/0279 |
| 2018/0154349 A1* | 6/2018 | Habbal | G01N 35/1011 |

FOREIGN PATENT DOCUMENTS

| | | |
|---|---|---|
| EP | 0513618 A2 | 11/1992 |
| EP | 0 801 309 A2 | 10/1997 |
| EP | 2034319 A2 | 3/2009 |
| JP | S63-313575 A | 12/1988 |
| JP | H04-244239 A | 9/1992 |
| JP | 2003-530210 A | 10/2003 |
| JP | 2005-110687 A | 4/2005 |
| JP | 2006-025771 A | 2/2006 |
| JP | 2009-034013 A | 2/2009 |
| JP | 2010-107352 A | 5/2010 |
| JP | 2011-115759 A | 6/2011 |
| JP | 2012-154649 A | 8/2012 |
| JP | 2013-102723 A | 5/2013 |
| WO | 2008/088065 A1 | 7/2008 |
| WO | 2008/156113 A1 | 12/2008 |

OTHER PUBLICATIONS

International Search Report issued in PCT/JP2014/065970; dated Aug. 19, 2014.

* cited by examiner

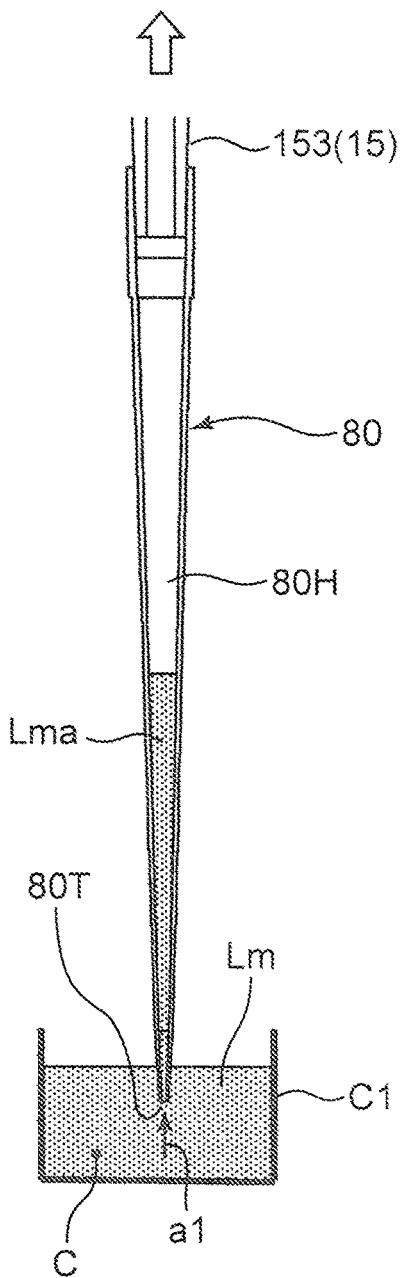
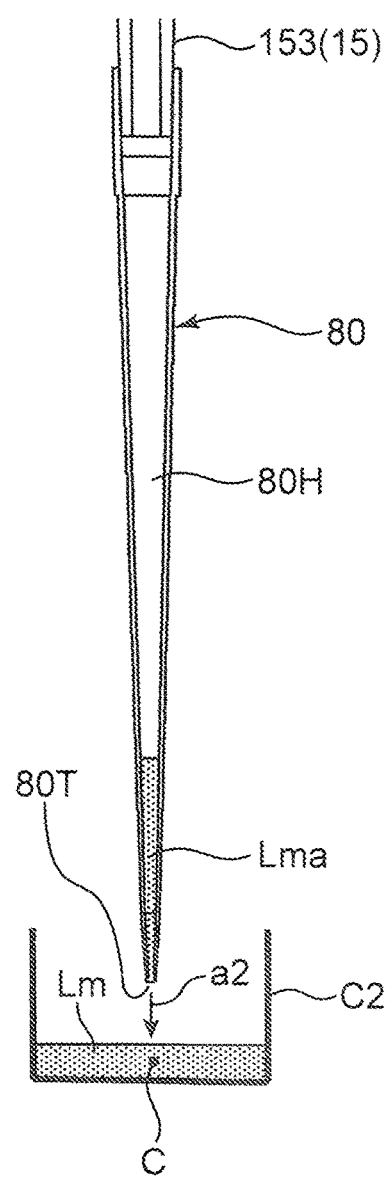

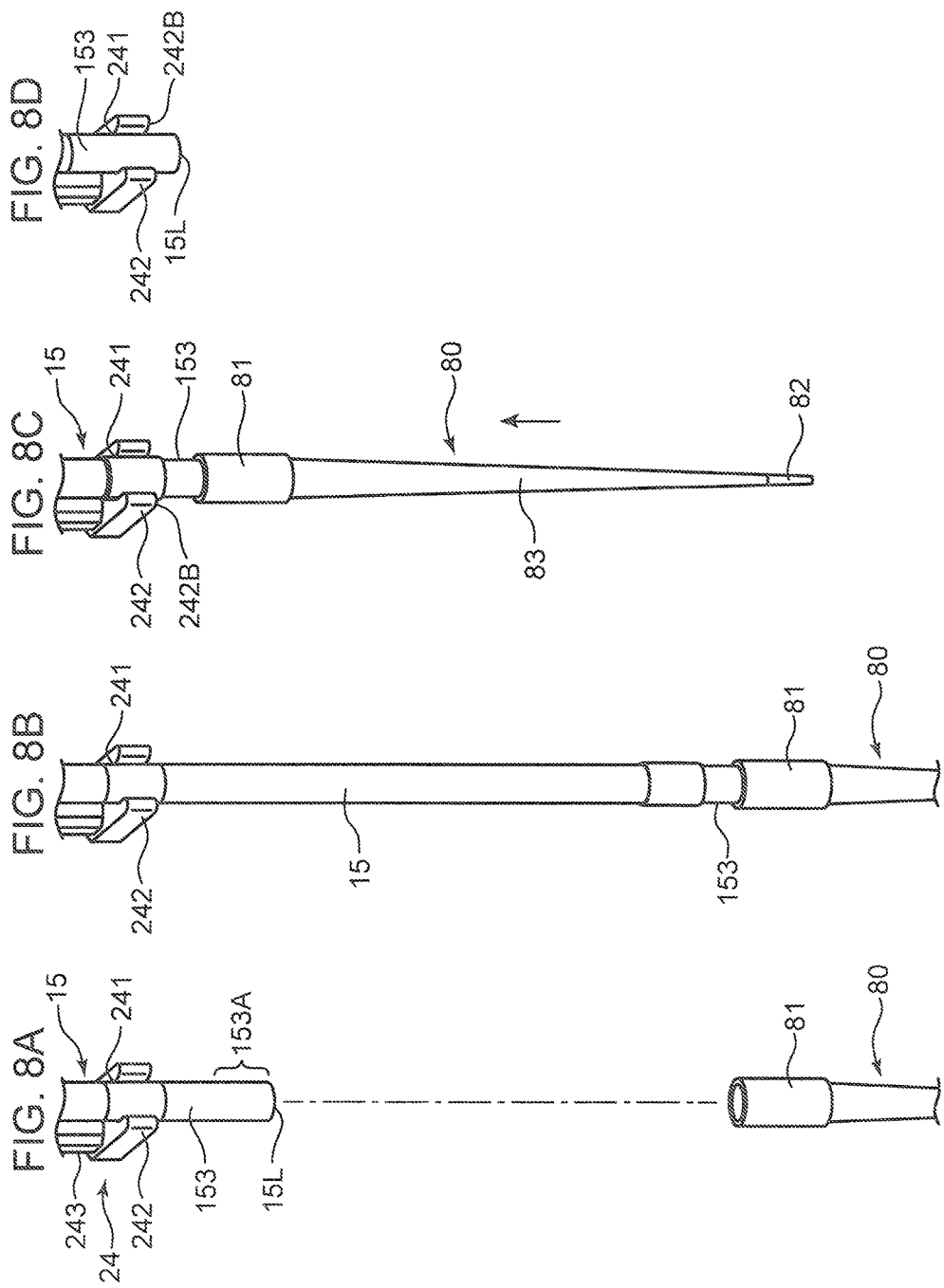

HEAD DEVICE FOR MOUNTING DISPENSING TIP THEREON, AND MOVEMENT DEVICE USING SAME

CROSS REFERENCE TO RELATED APPLICATION

This application claims benefit of priority to International Patent Application No. PCT/JP2014/065970 filed Jun. 17, 2014, the entire content of which is incorporated herein by reference.

TECHNICAL FIELD

The present invention relates to a head device to which a dispensing tip configured to suck liquid containing an object such as cell aggregates and discharge the sucked liquid is mounted, and also relates to a movement device for an object using the head device.

BACKGROUND

In facilities for research on cells, the dispensing process of extracting a proper amount of a cell culture solution containing a large amount of dispersed cell aggregates from a tube storing the cell culture solution and moving the cell culture solution to another dish is performed. For such a process, a dispensing tip configured to suck the cell culture solution from the tube and discharge the cell culture solution to another dish is used. In the dish, a process of sorting cell aggregates having a desired size from the cell culture solution containing cell aggregates of various sizes and impurities is performed, for example.

Japanese Unexamined Patent Publication No. 2009-34013 discloses the technique of sucking cell aggregate, which is a moving object, from a dispensing well by using a suction tip (a micropipette) and discharging the cell aggregate to a petri dish. Cell aggregates are held in liquid, and a tip end opening of the suction tip is dipped in the liquid during the above-described suction. Thus, there is a case where such a suction tip needs to be disposed after completion of a single process of suction and discharge.

It has been demanded for the process of moving an object to highly automate a series of operation including suction and discharge of the object by the dispensing tip. However, in a current situation, such automation has been only developed to such an extent that the dispensing tip is manually operated or that only the mechanism for generating suction force is additionally attached to the dispensing tip. For this reason, it cannot be said that the working efficiency of the movement process described above is favorable in the current situation.

SUMMARY

The present invention is intended to provide a head device for which the process of sucking an object by a dispensing tip and discharging the sucked object by the dispensing tip can be highly automated and a movement device for an object using the head device.

A head device for mounting a dispensing tip according to an aspect of the present invention is a head device to which a dispensing tip configured to suck liquid containing an object and discharge the sucked liquid is mounted. Such a head device includes a piston member, a first shaft member engaging with the piston member to move the piston member in an up-down direction, a tubular rod including a tubular space having a cylinder space in which the piston member is housed to move in the up-down direction and including, at a lower end thereof, a tip mounting portion into which a base end portion of the dispensing tip is fitted, a first frame equipped with the first shaft member and the tubular rod, a second shaft member engaging with the first frame to move the first frame in the up-down direction, a second frame equipped with the second shaft member and including a guide portion configured to guide movement of the tubular rod in the up-down direction in association with the movement of the first frame in the up-down direction, and a shaft controller configured to control operation of the first and second shaft members. The shaft controller executes, in the state in which the dispensing tip is mounted to the tip mounting portion, the first control of controlling the first shaft member such that the dispensing tip sucks and discharges the liquid by the movement of the piston member in the up-down direction, and the second control of controlling the second shaft member such that the guide portion and the base end portion of the dispensing tip come into contact with each other by upward movement of the first frame to detach the dispensing tip from the tip mounting portion.

A movement device according to another aspect of the present invention includes the head device for mounting the dispensing tip as described above, a first container configured to store an object, a second container configured to receive the object, and a head movement mechanism configured to move, in the horizontal direction, the head device between the first and second containers.

The objective, features, and advantageous effects of the present invention are more clarified from the following detailed description and the attached drawings.

BRIEF DESCRIPTION OF THE DRAWINGS

FIG. 7A is a schematic view of a suction operation of a cell culture solution by the dispensing tip, and FIG. 7B is a schematic view of a discharge operation of the cell culture solution by the dispensing tip.

FIGS. 8A to 8D are perspective views for describing the operation of mounting/detaching the dispensing tip to/from the head.

DETAILED DESCRIPTION

An embodiment of a head device 1 for mounting a dispensing tip according to the present invention will be described below in detail with reference to the drawings. In this embodiment, the case where an object to be sucked and discharged by a dispensing tip is organism-derived cells, particularly a cell culture solution containing cell aggregates, will be described. Note that liquid is not limited to the cell culture solution, and may be medical liquid, food industrial liquid, and manufacturing industrial liquid containing various types of objects, for example.

Figure 1:
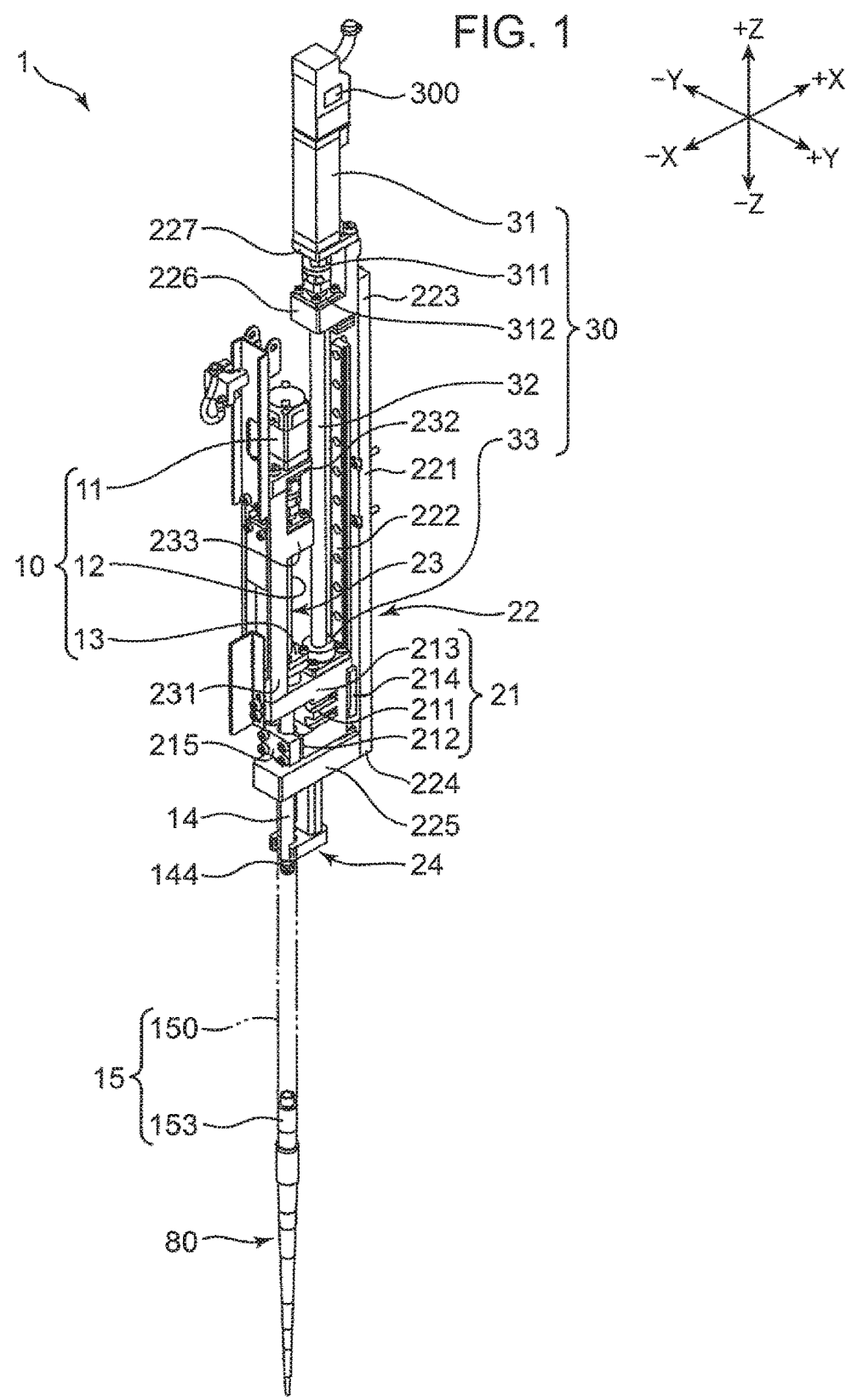
FIG. 1 is a perspective view of an outer appearance of a head device of an embodiment of the present invention.
Figure 2:
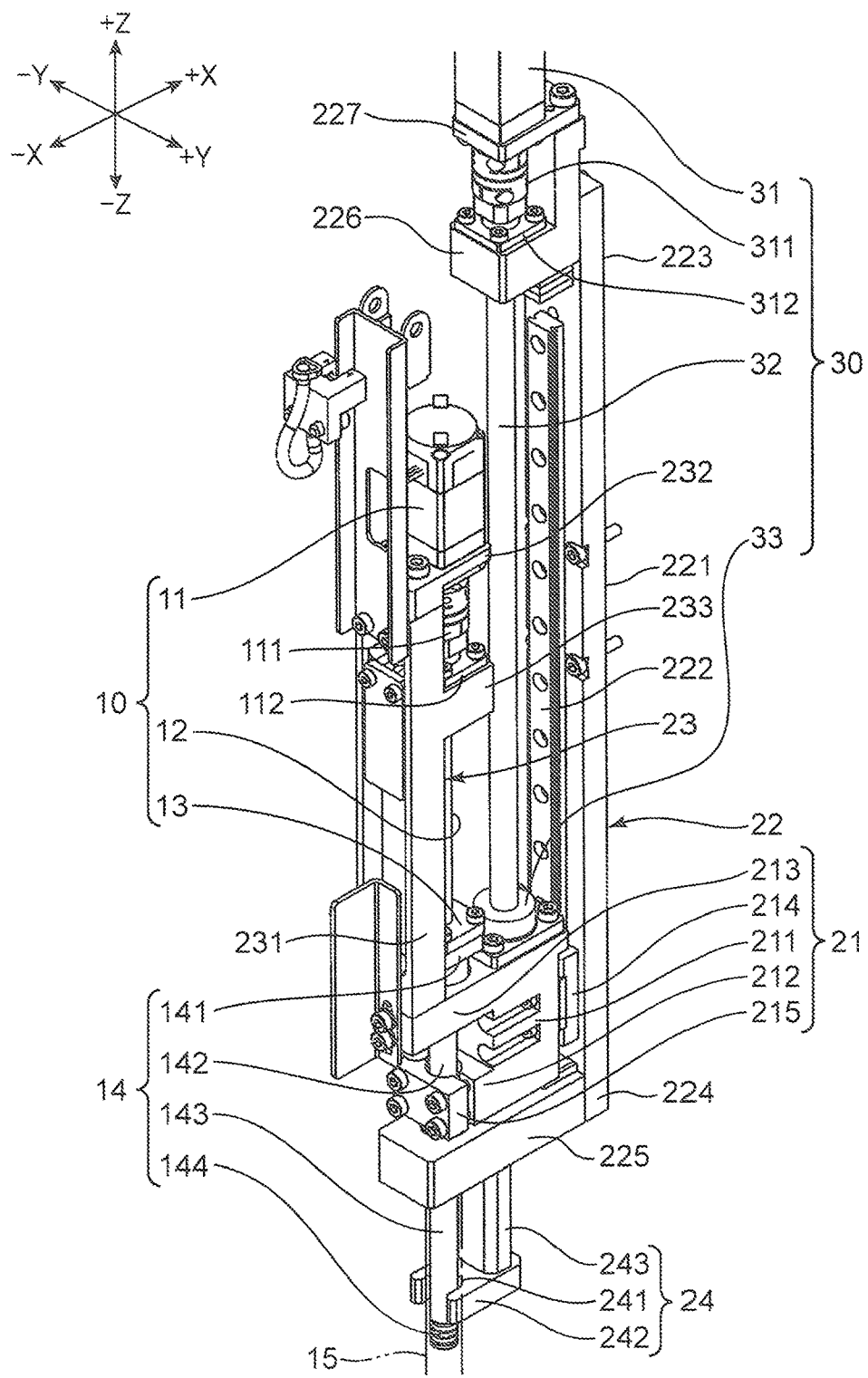
FIG. 2 is an enlarged perspective view of a main portion of FIG. 1.
Figure 3:
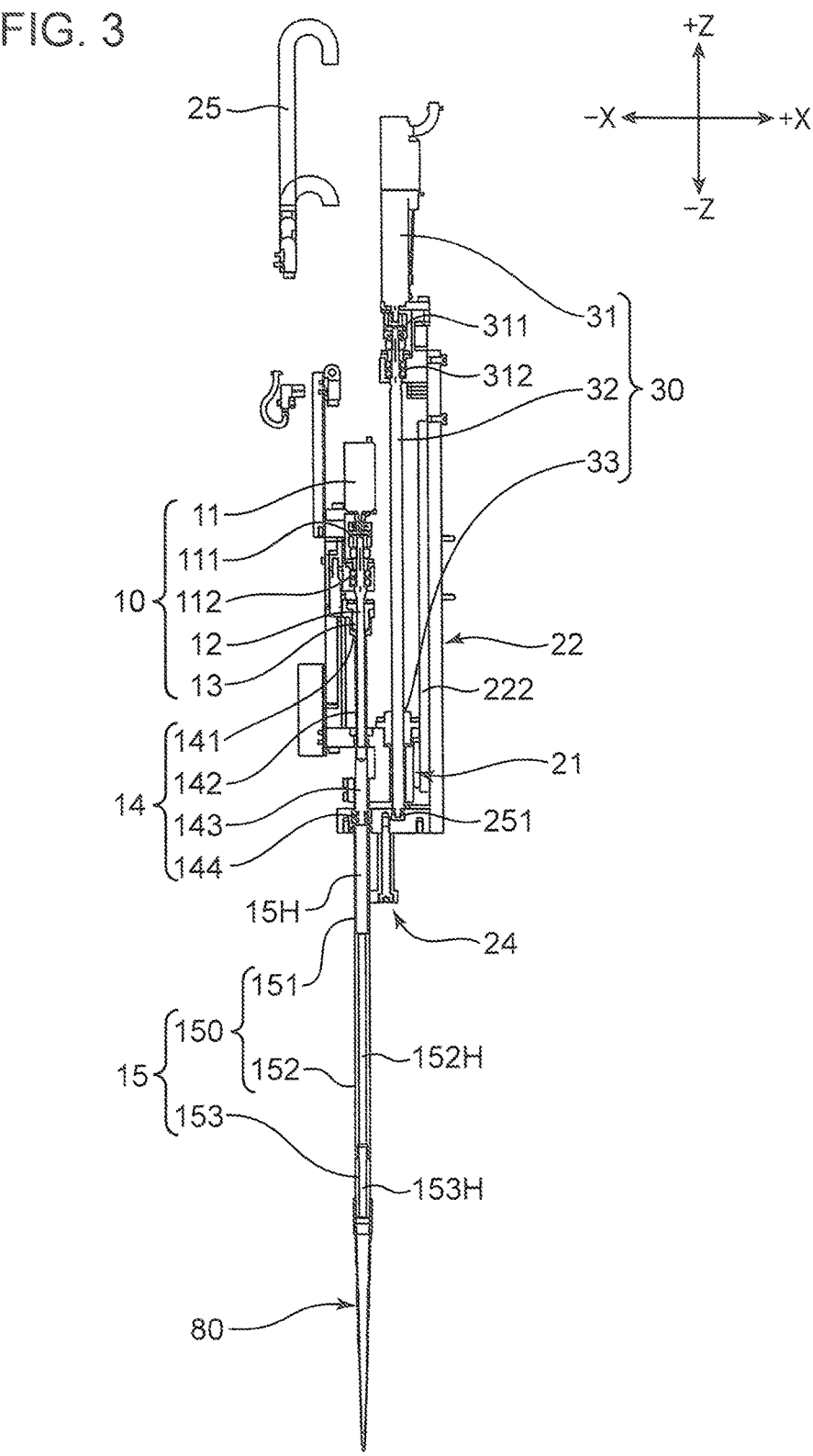
FIG. 3 is a sectional side view of the head device.

FIG. 1 is a perspective view of an outer appearance of the head device 1 of the embodiment of the present invention, FIG. 2 is an enlarged perspective view of a main portion of FIG. 1, and FIG. 3 is a sectional side view of the head device 1. The head device 1 is a device to which a dispensing tip 80 configured to suck a cell culture solution (liquid containing an object) containing cell aggregates and discharge the sucked cell culture solution is mounted. The head device 1 includes a first ball screw device 10 (a first shaft member), a piston member 14 configured to move in an up-down direction (a Z direction) by the first ball screw device 10, a head 15 (a tubular rod) to which the dispensing tip 80 is mounted, a first frame 21 equipped with the first ball screw device 10 and the head 15, a second ball screw device 30 (a second shaft member) configured to move the first frame 21 in the up-down direction, and a second frame 22 equipped with the second ball screw device 30.

The first ball screw device 10 engages with the piston member 14 to move the piston member 14 in the up-down direction. The first ball screw device 10 includes a first motor 11, a coupling 111, an upper bearing 112, a first threaded shaft 12, and a first nut member 13, these components being arranged in the Z direction. The first motor 11 is a motor configured to generate rotary drive force for rotating the first threaded shaft 12 forward and backward about an axis. The coupling 111 is a member configured to couple an output shaft of the first motor 11 and an upper end of the first threaded shaft 12 together. The upper bearing 112 is configured to rotatably support the upper end of the first threaded shaft 12. The first threaded shaft 12 extends in the Z direction, and is provided with an external thread carved at a peripheral surface of the first threaded shaft 12. The first nut member 13 has an inner surface provided with an internal thread, and engages with the first threaded shaft 12. When the first threaded shaft 12 rotates forward or backward, the first nut member 13 moves upward (+Z) or downward (−Z). The piston member 14 engages with such a first nut member 13.

Figure 10:
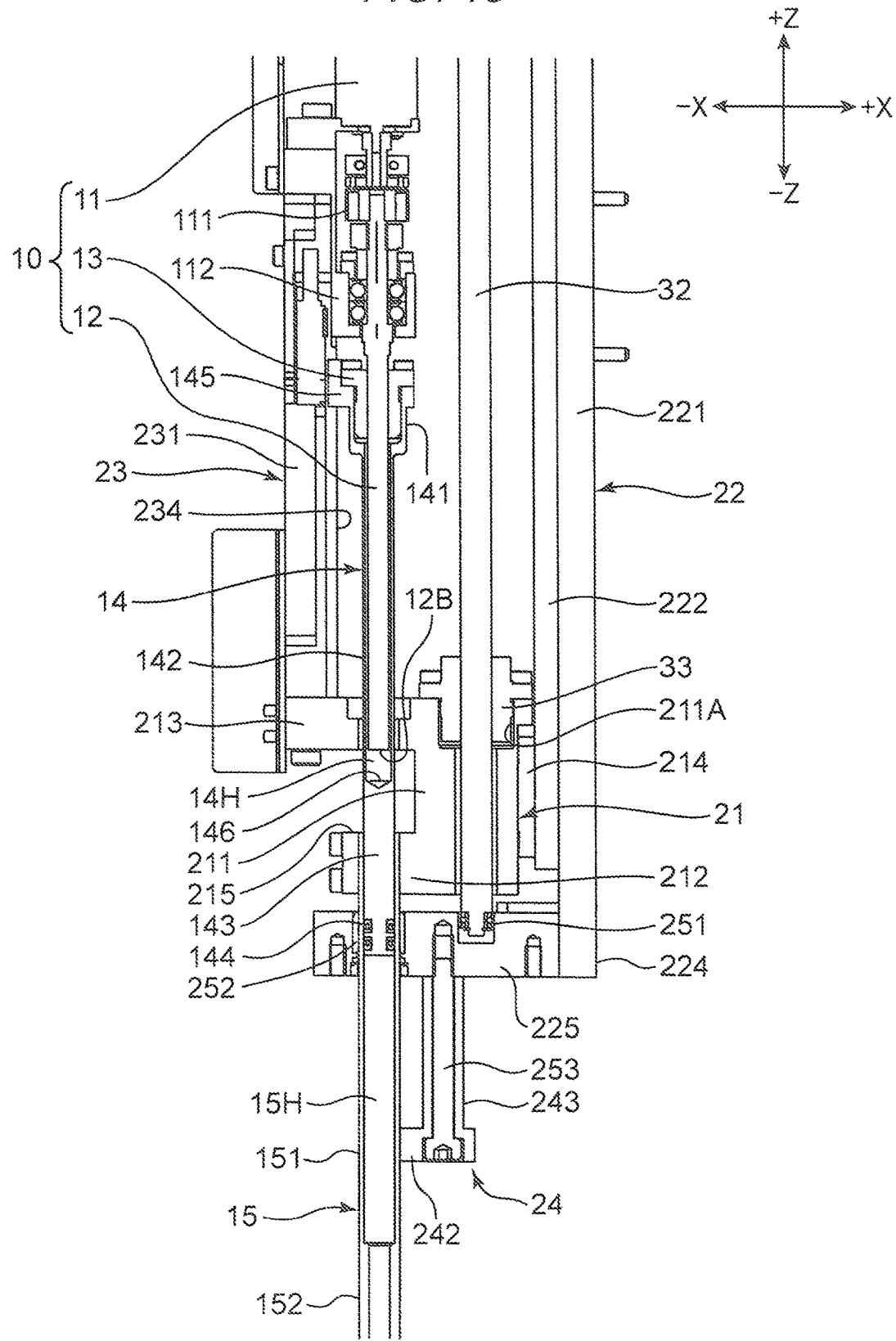
FIG. 10 is a longitudinal sectional view of the head device in the state of FIG. 9.

The piston member 14 is a member elongated in the Z direction and including an upper end portion 141, a lower end portion 143, and an intermediate portion 142 positioned between the upper end portion 141 and the lower end portion 143. Referring to FIG. 10 as an enlarged longitudinal sectional view of a main portion of FIG. 3, the upper end portion 141 is a cylindrical portion having a greater diameter than those of the intermediate portion 142 and the lower end portion 143, and has an inner peripheral surface provided with an engagement portion (a threaded portion) fixed to the first nut member 13. The first nut member 13 includes a tubular portion on the −Z side, as well as including a flange portion on the +Z side. In the state in which the tubular portion is fitted into the cylinder of the upper end portion 141 and the flange portion is held on an upper surface of the upper end portion 141, the first nut member 13 is screwed to the upper end portion 141. Thus, the piston member 14 moves in the up-down direction simultaneously with movement of the first nut member 13 in the up-down direction.

The lower end portion 143 is a circular columnar portion housed in a later-described cylinder space 15H of the head 15, and has a peripheral surface provided with a seal member 144. The seal member 144 is a resin seal ring, and is fitted into a seal groove formed at a peripheral surface of the piston member 14 in the vicinity of a lower end surface of the piston member 14. The intermediate portion 142 is a cylindrical portion having the same outer diameter as that of the lower end portion 143, and has, on the inside thereof, a housing space 14H in which the first threaded shaft 12 is housed. The housing space 14H is a circular columnar space extending in the Z direction, and has an inner diameter slightly greater than the outer diameter of the first threaded shaft 12. In the state in which the first nut member 13 has moved downward (FIG. 1 and FIG. 2), the first threaded shaft 12 is fitted relatively shallow in the housing space 14H (also see FIG. 12). On the other hand, in the state in which the first nut member 13 has moved upward (FIG. 3 and FIG. 10), the first threaded shaft 12 is fitted relatively deep in the housing space 14H.

The head 15 is a cylindrical member fixed to the first frame 21 and being unmovable on the piston member 14. The head 15 includes a head body 150 (a rod body) having first and second portions 151, 152 continuously extending in the up-down direction, and a replaceable portion 153 detachably mounted to a lower end of the head body 150.

The first portion 151 has, on the inside thereof, the cylinder space 15H in which the lower end portion 143 of the piston member 14 is housed to move in the up-down direction. The cylinder space 15H is a circular columnar space having an inner diameter slightly greater than the outer diameter of the lower end portion 143. The seal member 144 closely contacts and slides on an inner wall surface of the first portion 151 defining the cylinder space 15H. The second portion 152 has, on the inside thereof, a tubular space 152H communicating with the cylinder space 15H and having a smaller inner diameter than that of the cylinder space 15H. The replaceable portion 153 has, on the inside thereof, a tubular space 153H communicating with the tubular space 152H and the cylinder space 15H, and an upper end of the replaceable portion 153 is screwed to a lower end of the second portion 152. An outer peripheral surface portion of the replaceable portion 153 in the vicinity of a lower end thereof is a tip mounting portion 153A into which the dispensing tip 80 is fitted (see FIG. 6).

The second ball screw device 30 is a shaft member configured to move, in the up-down direction, the first frame 21 equipped with the first ball screw device 10 and the head 15. The second ball screw device 30 includes a second motor 31, a coupling 311, an upper bearing 312, a second threaded shaft 32, and a second nut member 33, these components being arranged in the Z direction.

The second motor 31 is a motor configured to generate rotary drive force for rotating the second threaded shaft 32 forward and backward about an axis. The coupling 311 is a member configured to couple an output shaft of the second motor 31 and an upper end of the second threaded shaft 32 together. The upper bearing 312 is configured to rotatably support the upper end of the second threaded shaft 32. The second threaded shaft 32 extends in the Z direction, and is provided with an external thread carved at a peripheral surface of the second threaded shaft 32. The second nut member 33 has an inner surface provided with an internal thread, and engages with the second threaded shaft 32. When the second threaded shaft 32 rotates forward or backward, the second nut member 33 moves upward (+Z) or downward (−Z). The first frame 21 is fixed to the second nut member 33.

The first frame 21 serves the function of holding the head 15 in a fixed manner, the function of operating along with the second nut member 33 to move the head 15 in the up-down direction, and the function of holding the first ball screw device 10. The first frame 21 includes a main frame portion 211, a lower frame portion 212 protruding in a −X direction at a lower part of the main frame portion 211, an upper frame portion 213 protruding in the −X direction at an upper part of the main frame portion 211, and a guiding target portion 214 disposed at the side of the main frame portion 211 in a +X direction.

As illustrated in FIG. 10, the main frame portion 211 is provided with a hole through which the second threaded shaft 32 penetrates in the up-down direction. An upper end of the main frame portion 211 is provided with a holding hole 211A for holding the second nut member 33. The second nut member 33 includes a tubular portion on the −Z side, as well as including a flange portion on the +Z side. In the state in which the tubular portion is fitted into the holding hole 211A and the flange portion is held on an upper surface of the main frame portion 211, the second nut member 33 is screwed to the main frame portion 211. Thus, the first frame 21 moves in the up-down direction simultaneously with movement of the second nut member 33 in the up-down direction.

The lower frame portion 212 is a portion configured to hold an upper end portion of the head 15 in a fixed manner. The −X side surface of the lower frame portion 212 is provided with a longitudinal groove having a semicircular cross section to house the +X side half of the head 15. A holding piece 215 provided with a similar longitudinal groove having a semicircular cross section is additionally provided at the −X side half of the head 15. In the state in which the longitudinal grooves of the lower frame portion 212 and the holding piece 215 sandwich the upper end portion of the head 15, the lower frame portion 212 is screwed and fixed to the holding piece 215, and as a result, the head 15 is fixed to the first frame 21.

The upper frame portion 213 is provided with a hole through which the intermediate portion 142 of the piston member 14 penetrates in the up-down direction. A holding frame 23 configured to hold the first ball screw device 10 is provided to stand on the −X side end portion of the upper frame portion 213. As illustrated in FIG. 2, the holding frame 23 includes a vertical frame 231 and upper and lower frames 232, 233 provided to protrude from an upper end of the vertical frame 231 in the +X direction. A guide rail 234 (FIG. 10) extending in the up-down direction is attached to the vertical frame 231. The guide rail 234 engages with a guiding target portion 145 additionally provided at the upper end portion 141 of the piston member 14. When the first nut member 13 moves up and down, the piston member 14 moves up and down while being guided by the guide rail 234. The first motor 11 is fixed to the upper frame 232. The upper bearing 112 is fixed to the lower frame 233.

The second frame 22 serves the function of holding the second ball screw device 30, the function of guiding movement of the first frame 21 in the up-down direction, and the function of guiding movement of the head 15 in the up-down direction. The second frame 22 includes a longitudinal frame 221, a transverse frame 225 provided to protrude from a lower end 224 of the longitudinal frame 221 in the −X direction, and an arm member 24 (a guide portion) provided to protrude from a lower surface of the transverse frame 225 in the −Z direction.

The longitudinal frame 221 is a rectangular frame extending in the up-down direction, and a guide rail 222 extending in the up-down direction is attached to the −X side surface of the longitudinal frame 221. The guiding target portion 214 of the first frame 21 as described above is fitted into the guide rail 222. Thus, in driving of the second ball screw device 30, the first frame 21 can move in the up-down direction while being guided along the guide rail 222. An L-shaped frame 226 configured to hold the upper bearing 312 is attached to an upper end 223 of the longitudinal frame 221. A holding frame 227 configured to hold the second motor 31 is fixed to an upper end of the L-shaped frame 226.

The transverse frame 225 is a rectangular frame extending in the X direction. The transverse frame 225 includes a bearing portion 251 configured to rotatably support a lower end of the second threaded shaft 32, and a through-hole 252 through which the head 15 penetrates in the up-down direction. When the first frame 21 and the head 15 together move in the up-down direction, swinging of the head 15 is restricted by an inner wall surface of the through-hole 252. The arm member 24 is, with a screw 253 (FIG. 10), assembled with a lower surface of the transverse frame 225.

The arm member 24 is configured to guide movement of the head 15 (the head body 150) in the up-down direction in association with movement of the first frame 21 in the up-down direction. Moreover, the arm member 24 also serves the function of detaching, from the head 15, the dispensing tip 80 mounted to the head 15. Such a point will be described in detail later. The arm member 24 includes a guide plate 242 having a U-shaped guide recess 241 opening in the −X direction, and a vertical arm 243.

The guide plate 242 is a plate member extending in the horizontal direction. The opening width of the guide recess 241 in a Y direction and the inner diameter of a semicircular bottom surface of a U-shaped opening are slightly greater than the outer diameter of the head 15 having the cylindrical shape. Thus, the guide recess 241 can be laterally fitted onto the head 15. The vertical arm 243 is a plate member protruding downward from the lower surface of the transverse frame 225. The end portion of the guide plate 242 in the +X direction is fixed to a lower end surface of the vertical arm 243 with the screw 253. The screw 253 upwardly penetrates the guide plate 242 and the vertical arm 243 from below, and is screwed into a threaded hole formed at the lower surface of the transverse frame 225.

Figure 4:
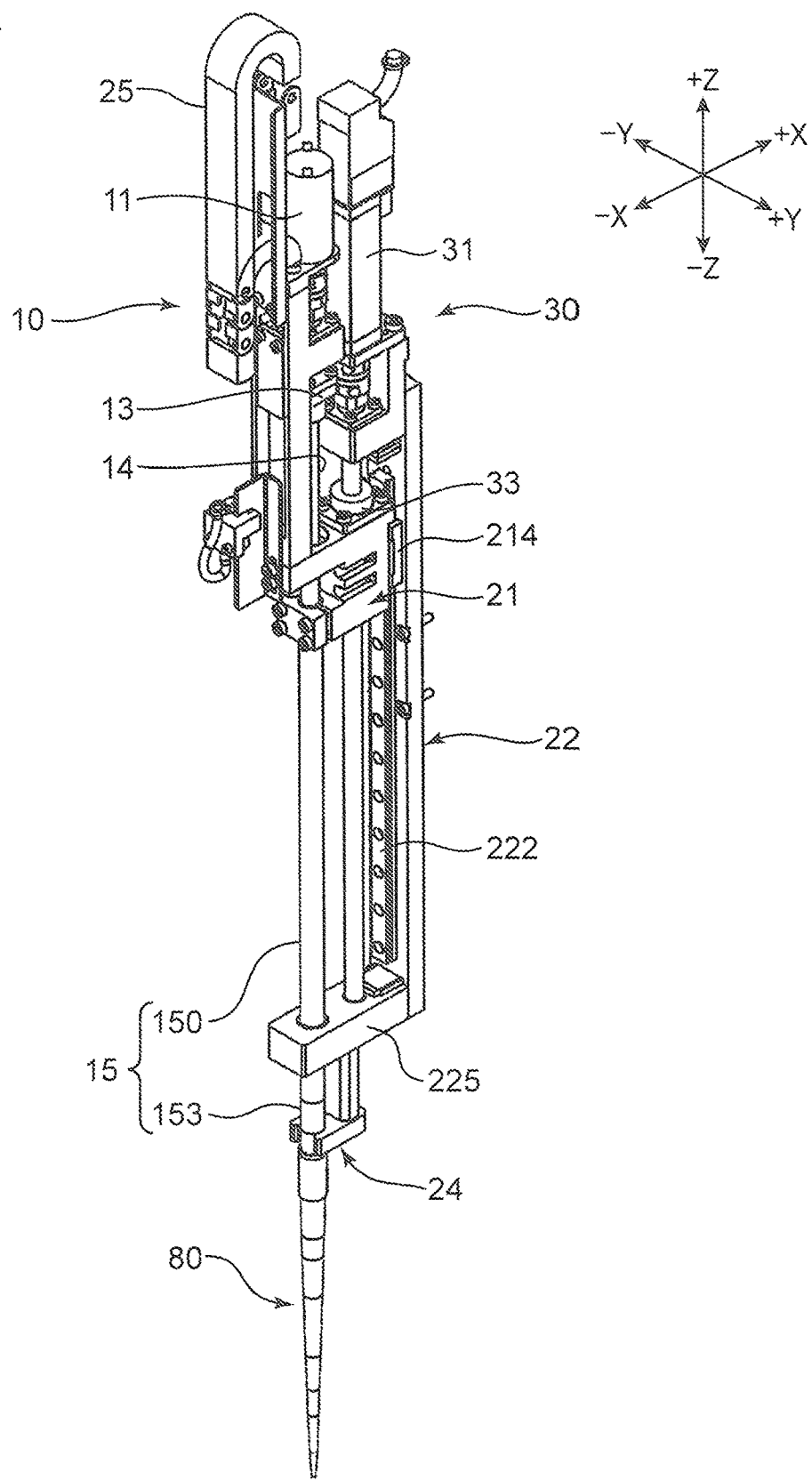
FIG. 4 is a perspective view of the head device in the state in which a head (a tubular rod) is lifted in a Z direction.

FIG. 4 is a perspective view of the head device 1 in the state in which the head 15 is lifted in the +Z direction. In this state, the first frame 21 is lifted relative to the second frame 22 by driving of the second ball screw device 30. That is, the first frame 21 is positioned in the vicinity of a +Z upper limit of a movable area along the guide rail 222. Accordingly, the first ball screw device 10 and the head 15 held by the first frame 21 are also lifted. In FIG. 4, a bending protection member 25 configured to protect a power distribution cable of the first motor 11 is additionally provided. The bending protection member 25 is a portion upwardly curved in a raised shape, and is deformable along with upward and downward movement of the first frame 21.

The Z-direction height position of the dispensing tip 80 mounted to a lower end of the head 15 is also lifted by lifting of the head 15. Specifically, an upper end of the dispensing tip 80 is positioned immediately near a lower side of the arm member 24. The dispensing tip 80 is disposed at such a height position when suction of the cell culture solution containing the dispersed cell aggregates is completed and the head device 1 moves to a dish arrangement position as a discharge destination in an XY direction, for example.

Figure 5:
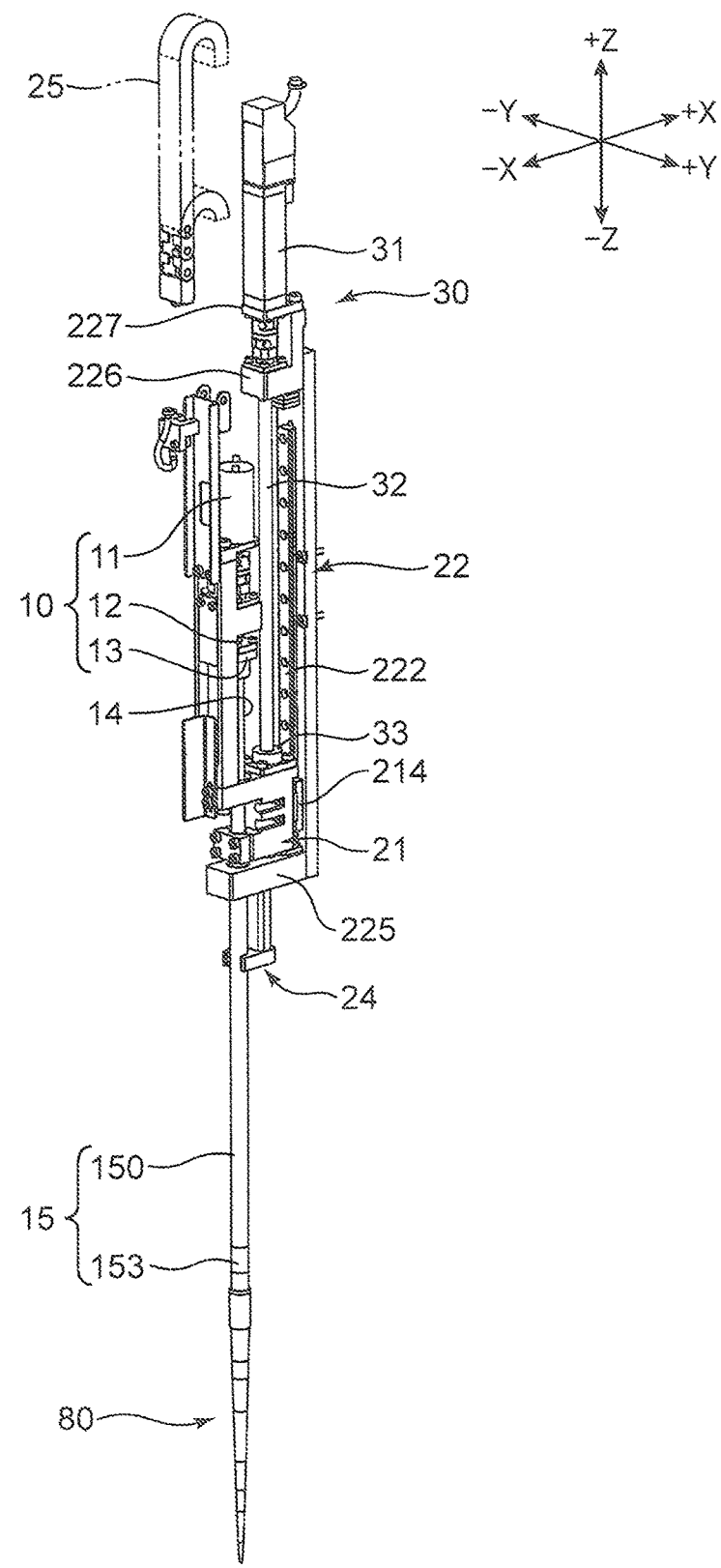
FIG. 5 is a perspective view of the head device in the state in which the head is lowered in the Z direction.

FIG. 5 is a view in the state in which the head 15 is lowered in the −Z direction. In this state, the first frame 21 is positioned in the vicinity of a −Z lower limit of the movable area along the guide rail 222 by driving of the second ball screw device 30, and is close to the transverse frame 225 of the second frame 22. Accordingly, the first ball screw device 10 and the head 15 are also lowered. The head 15 is in the state of greatly protruding downward from the transverse frame 225.

The height position of the dispensing tip 80 in the Z direction is also lowered by downward movement of the head 15. The dispensing tip 80 is disposed at such a lowered position when the cell culture solution is, by the dispensing tip 80, sucked from a tube storing the cell culture solution or when the sucked cell culture solution is discharged to another dish, for example.

Figure 6:
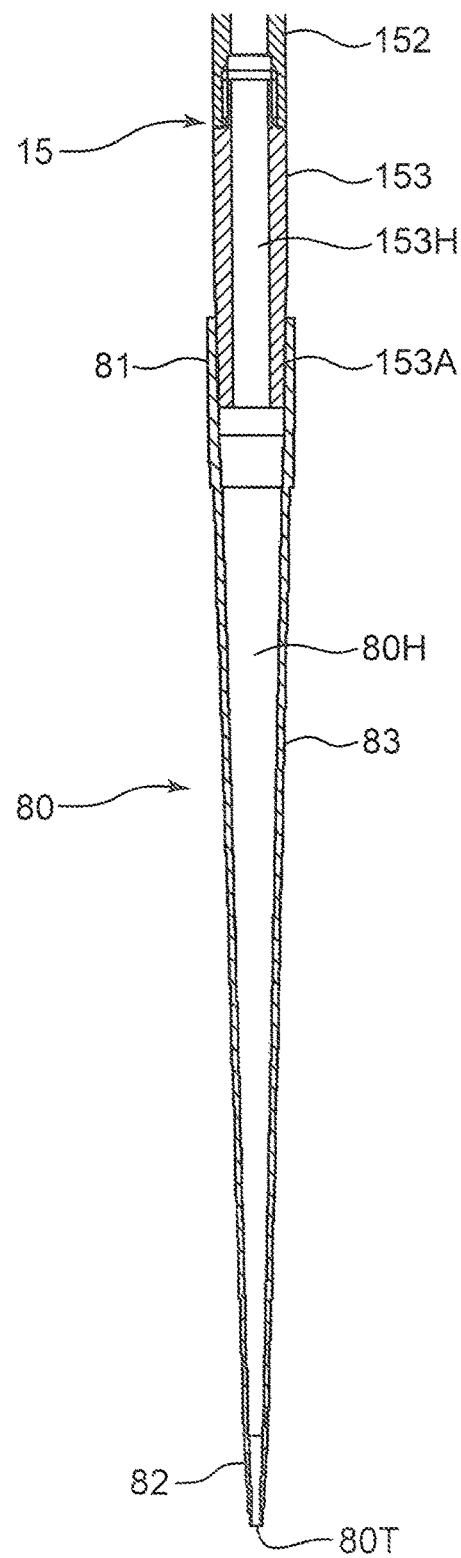
FIG. 6 is a longitudinal sectional view of a dispensing tip.

Next, the dispensing tip 80 mounted to the head 15 in the present embodiment will be described. FIG. 6 is a longitudinal sectional view of the dispensing tip 80 in the state in which the dispensing tip 80 is mounted to the head 15. The dispensing tip 80 is an elongated tubular member. The dispensing tip 80 includes a base end portion 81 fitted onto the head 15 (the replaceable portion 153), a tip end portion 82 having a lower edge provided with an opening 80T through which the cell culture solution is sucked and discharged, and an intermediate portion 83 extending between the base end portion 81 and the tip end portion 82. The intermediate portion 83 is in such a tapered shape that the outer diameter of the intermediate portion 83 gradually decreases from the base end portion 81 to the tip end portion 82. Note that an air filter may be incorporated in the base end portion 81. The dispensing tip 80 can be mounted/detached to/from the tip mounting portion 153A of the replaceable portion 153. The tip mounting portion 153A is the outer peripheral surface portion of the replaceable portion 153 in the vicinity of the lower end thereof.

A tubular space 80H in which the liquid containing the object can be housed is formed in the dispensing tip 80. The tubular space 80H communicates with the tubular space 153H in the replaceable portion 153 of the head 15, the tubular space 152H in the second portion 152, and the cylinder space 15H in the first portion 151. Thus, suction force is generated in the tubular space 80H when the piston member 14 moves upward, and discharge force is generated in the tubular space 80H when the piston member 14 moves downward. The suction force causes the dispensing tip 80 to suck the cell culture solution through the opening 80T, and the discharge force causes the dispensing tip 80 to discharge the sucked cell culture solution through the opening 80T.

FIG. 7A and FIG. 7B are schematic views of the operation of sucking and discharging a cell culture solution Lm containing a cell aggregate C by the dispensing tip 80. The example will be described herein, in which the dispensing tip 80 sucks the cell culture solution Lm (the cell aggregate C) stored in a first container C1, and discharges the sucked cell culture solution Lm to a second container C2. FIG. 7A illustrates the operation of sucking the cell culture solution Lm from the first container C1 by the dispensing tip 80, and FIG. 7B illustrates the operation of discharging the sucked cell culture solution Lm to the second container C2 by the dispensing tip 80.

In the suction operation of FIG. 7A, positioning of the head device 1 is first performed such that the dispensing tip 80 is positioned above the first container C1. Subsequently, the head 15 is lowered by driving of the second ball screw device 30, as illustrated in FIG. 5. The head 15 is lowered until the opening 80T at a lower end of the dispensing tip 80 reaches below a liquid surface of the cell culture solution Lm stored in the first container C1. Then, the piston member 14 is, by driving of the first ball screw device 10, lifted to generate suction force in the tubular space 80H. Such suction force generates a suction liquid flow indicated by an arrow a1 in the vicinity of the opening 80T, and the cell culture solution Lm is sucked into the tubular space 80H. A reference character "Lma" in the figures indicates the cell culture solution sucked into the tubular space 80H. After such a suction operation, the head 15 is lifted by driving of the second ball screw device 30, as illustrated in FIG. 4.

In the discharging operation, the head device moves in the XY direction such that the dispensing tip is positioned above the second container. Subsequently, the head is lowered by driving of the second ball screw device. The head is lowered until the opening of the dispensing tip enters a cavity of the second container. Then, the piston member is, by driving of the first ball screw device, lowered to generate discharge force in the tubular space. Such discharge force discharges, through the opening, the cell culture solution held in the tubular space, and the cell culture solution is stored in the second container.

In the present embodiment, the operation of mounting the dispensing tip 80 to the head 15 and the operation of detaching the dispensing tip 80 from the head 15 are automated. FIGS. 8A to 8D are perspective views for describing the operation of mounting/detaching the dispensing tip 80 to/from the tip mounting portion 153A of the head 15 (the replaceable portion 153).

When mounting the dispensing tip 80 to the tip mounting portion 153A, the head 15 is positioned above the single dispensing tip 80 in a standing state, as illustrated in FIG. 8A. Then, the head 15 is lowered by driving of the second ball screw device 30. By such lowering, the tip mounting portion 153A of the head 15 is fitted into the base end portion 81 of the dispensing tip 80 as illustrated in FIG. 8B. FIG. 8C illustrates the state in which the head 15 to which the dispensing tip 80 is mounted is lifted by driving of the second ball screw device 30.

In the operation of sucking and discharging the cell culture solution by the dispensing tip 80, the second ball screw device 30 does not further lift the dispensing tip 80 from the state of FIG. 8C. However, in detachment of the dispensing tip 80 from the tip mounting portion 153A, the head 15 is further lifted upward as illustrated in FIG. 8D. When the head 15 is further lifted upward, a lower end surface of the guide plate 242 and an upper edge of the dispensing tip 80 come into contact with each other. By such contact, the dispensing tip 80 is gradually separated from the tip mounting portion 153A, and eventually, is detached from the tip mounting portion 153A.

Figure 9:
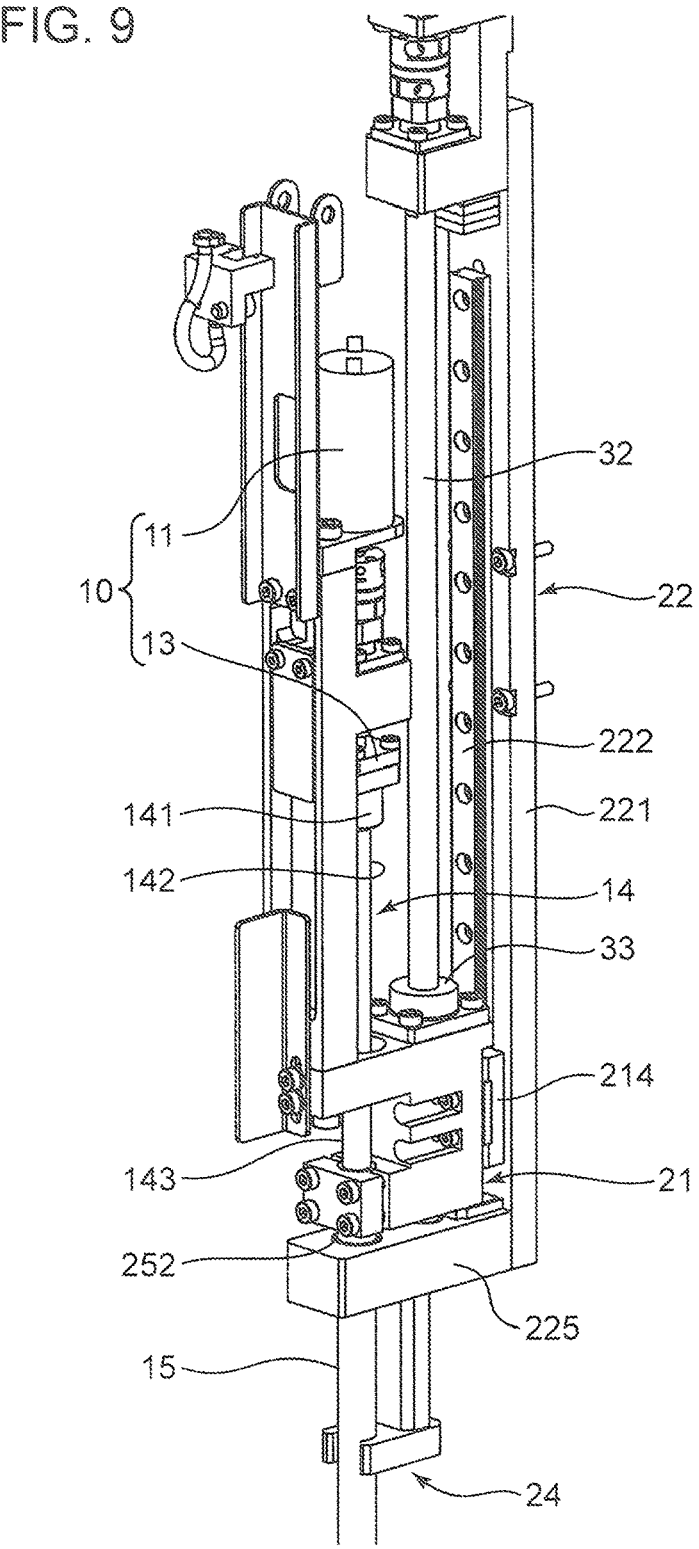
FIG. 9 is a perspective view of the head device in the state in which a piston member is lifted.
Figure 11:
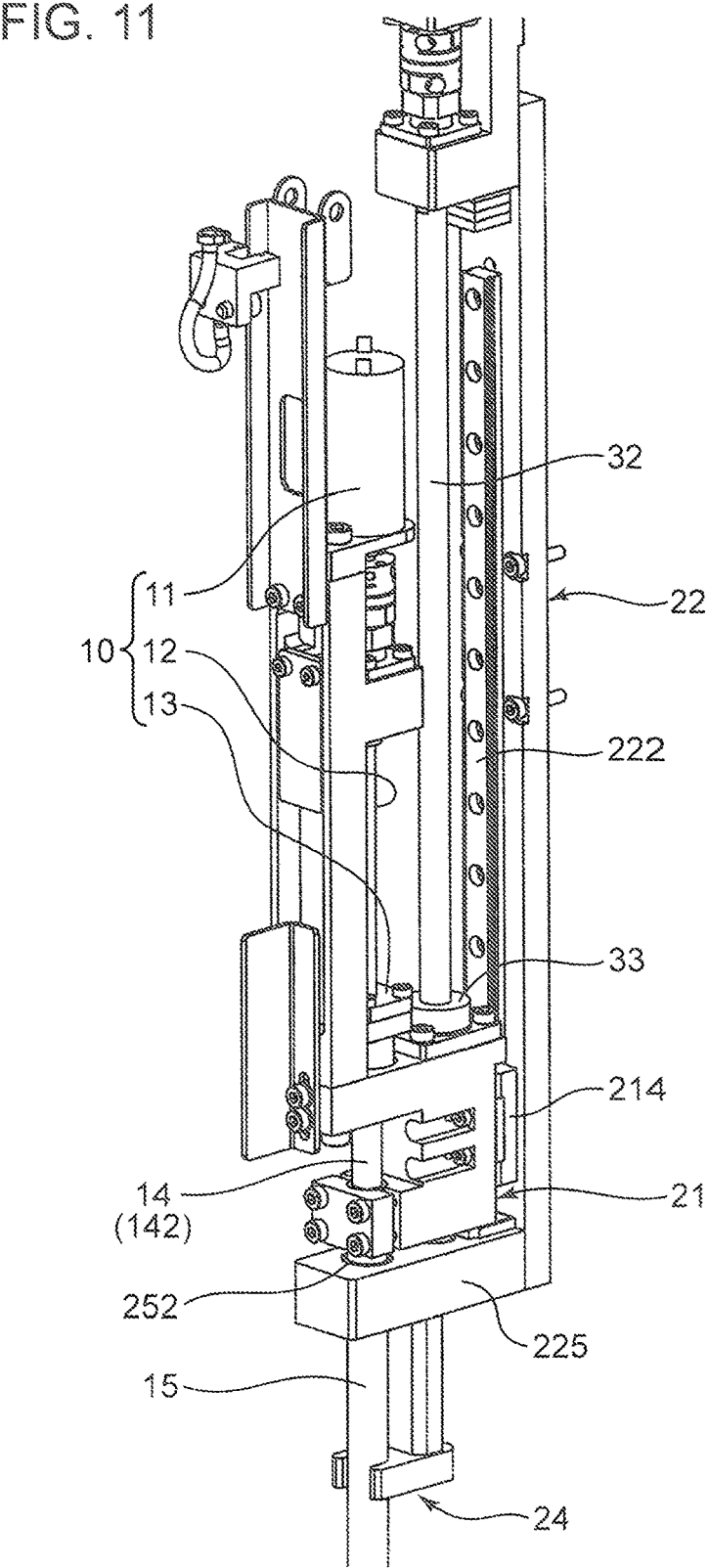
FIG. 11 is a perspective view of the head device in the state in which the piston member is lowered.

A detailed configuration realizing the operation of sucking and discharging liquid (the cell culture solution Lm) by the dispensing tip 80 as illustrated in FIG. 7A and FIG. 7B will be described with reference to FIG. 9 to FIG. 12. FIG. 9 is a perspective view of the head device 1 in the state in which the piston member 14 is lifted for the suction operation illustrated in FIG. 7A, and FIG. 10 is a longitudinal sectional view of the head device 1 in the state of FIG. 9. FIG. 11 is a perspective view of the head device 1 in the state in which the piston member 14 is lowered for the discharge operation illustrated in FIG. 7B, and FIG. 12 is a longitudinal sectional view of the head device 1 in the state of FIG. 11.

Referring to FIG. 9 and FIG. 10, the first threaded shaft 12 is, in the suction operation, rotatably driven by the first valve 11 such that the first nut member 13 moves upward. At this point, the first frame 21 is fixed at a lowermost position in the movable area thereof. When the first nut member 13 is lifted, the piston member 14 fixed to the first nut member 13 is lifted together. In this state, the housing space 14H of the piston member 14 functions as a relief hole of the first threaded shaft 12. The Z-direction length of the housing space 14H including the inner cylindrical space of the upper end portion 141 is set slightly longer than that of the first threaded shaft 12. FIG. 9 and FIG. 10 illustrate the state in which the first nut member 13 has moved to an uppermost position in a movable area along the first threaded shaft 12. In this state, the first threaded shaft 12 is fitted deep in the housing space 14H, and the distance between a lower end 12B of the first threaded shaft 12 and a bottom surface 146 of the housing space 14H is shortest.

Even when the piston member 14 is lifted as described above, the head 15 is unmovable. This is because the head 15 is held by the first frame 21 in the fixed manner. Thus, in association with lifting of the first nut member 13, the lower end portion 143 of the piston member 14 moves upward in the cylinder space 15H. Sealability between the lower end portion 143 and the cylinder space 15H is ensured by the seal member 144, and therefore, the cylinder space 15H is under negative pressure because of lifting of the lower end portion 143. Thus, suction force is generated in the tubular space 80H of the dispensing tip 80 communicating with the cylinder space 15H. Note that the degree of lifting of the piston member 14 is adjusted according to the amount of liquid sucked into the tubular space 80H.

Figure 12:
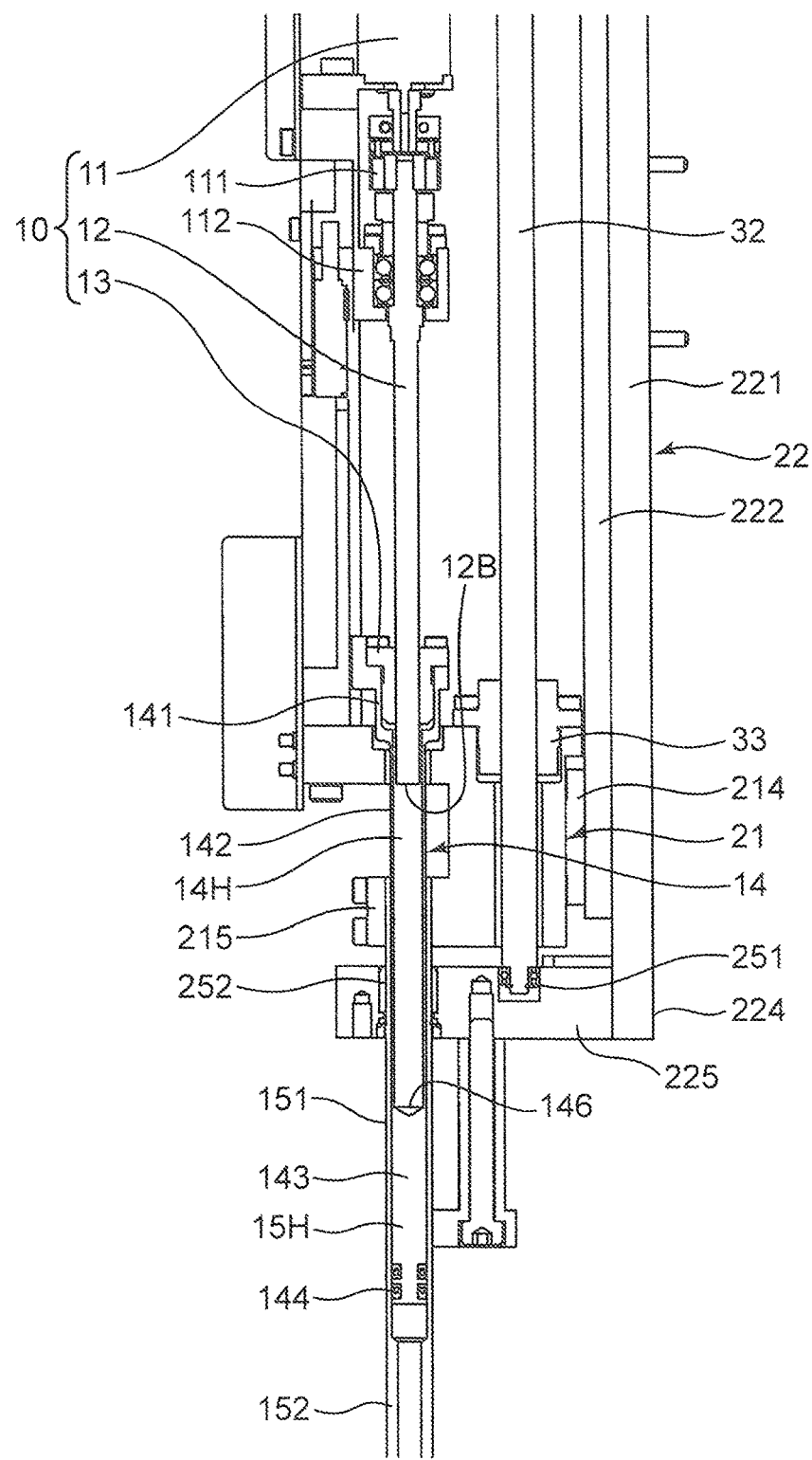
FIG. 12 is a longitudinal sectional view of the head in the state of FIG. 11.

Referring to FIG. 11 and FIG. 12, the first threaded shaft 12 is, in the discharge operation, rotatably driven by the first motor 11 such that the first nut member 13 moves downward. When the first nut member 13 is lowered, the piston member 14 integrated with the first nut member 13 is also lowered. At this point, the first threaded shaft 12 gradually moves out of the housing space 14H of the piston member 14. FIG. 11 and FIG. 12 illustrate the state in which the first nut member 13 has moved to a lowermost position in the movable area along the first threaded shaft 12. In this state, the first threaded shaft 12 is fitted at the most shallow position in the housing space 14H, and the distance between the lower end 12B of the first threaded shaft 12 and the bottom surface 146 of the housing space 14H is longest.

Thus, in association with lowering of the first nut member 13, the lower end portion 143 of the piston member 14 moves downward in the cylinder space 15H. In the case where the cell culture solution is present in the tubular space 80H of the dispensing tip 80, air in the cylinder space 15H is pressurized by lowering of the lower end portion 143. Thus, such pressing force discharges the cell culture solution held in the tubular space 80H from the dispensing tip 80.

Figure 13:
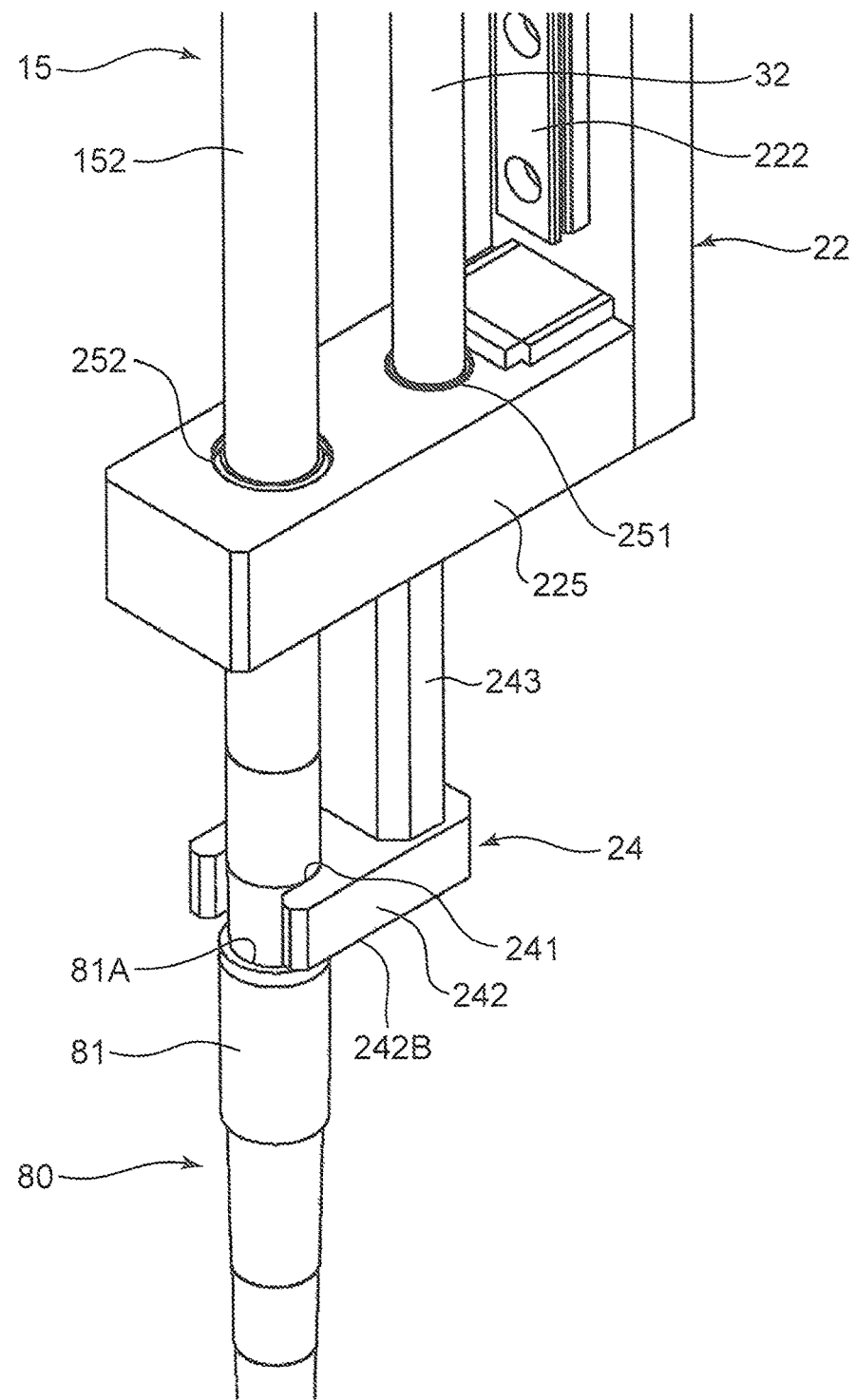
FIG. 13 is a perspective view of a state immediately before the dispensing tip is detached from the head by a guide portion.

Subsequently, a mechanism realizing the operation of detaching the dispensing tip 80 from the head 15 (the tip mounting portion 153A) will be described. FIG. 13 is a perspective view of a state immediately before the dispensing tip 80 is detached from the head 15 by the arm member 24. As already described, the guide plate 242 of the arm member 24 is the portion configured to guide movement of the head 15 in the up-down direction, and includes the guide recess 241 having the opening width slightly greater than the outer diameter of the head 15. The opening width of the guide recess 241 is a width smaller than the outer diameter of the dispensing tip 80 mounted to the tip mounting portion 153A. Thus, in the state of FIG. 13, a lower end surface 242B of the guide plate 242 and an upper edge 81A of the base end portion 81 of the dispensing tip 80 face each other.

When the head 15 is further lifted upward from the state of FIG. 13 by driving of the first ball screw device 10, the lower end surface 242B of the guide plate 242 begins to come into abutment (contact) with the upper edge 81A of the dispensing tip 80. The dispensing tip 80 is merely fitted onto the tip mounting portion 153A without bonding or the like. Thus, in association with lifting of the head 15, the upper edge 81A is pressed against the lower end surface 242B, and the base end portion 81 is gradually separated from the tip mounting portion 153A. After the lower end surface 242B has contact with the upper edge 81A, when the head 15 is lifted by the Z-direction length of the tip mounting portion 153A, the dispensing tip 80 is detached and dropped from the tip mounting portion 153A.

Figure 14:
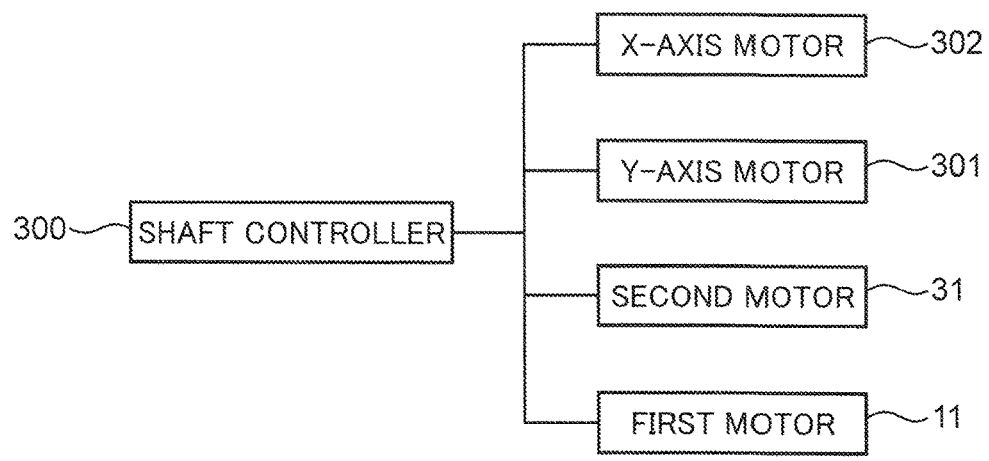
FIG. 14 is a block diagram of a control configuration of the head device.

FIG. 14 is a block diagram of a control configuration of the head device 1. The head device 1 includes a shaft controller 300 configured to control driving of the first ball screw device 10 and the second ball screw device 30 and to control movement of the head device 1 itself in the X direction, the Y direction, and the Z direction. Specifically, the shaft controller 300 controls the first and second motors 11, 31, as well as controlling an X-axis motor 302 and a Y-axis motor 301 (a head movement mechanism configured to move the head device 1 in the horizontal direction) not shown in the figures described above.

The shaft controller 300 executes the following first and second controls with the dispensing tip 80 being mounted to the tip mounting portion 153A of the head 15:

(First Control) the first ball screw device 10 is controlled such that the cell culture solution containing the cell aggregates is sucked and discharged through the dispensing tip 80 by movement of the piston member 14 in the up-down direction (see FIG. 7A, FIG. 7B, and FIG. 9 to FIG. 12); and (Second Control) the second ball screw device 30 is controlled such that the arm member 24 (the guide portion) and the base end portion 81 of the dispensing tip 80 come into contact with each other by upward movement of the first frame 21 to detach the dispensing tip 80 from the tip mounting portion 153A (see FIGS. 8A to 8D and FIG. 13).

Further, the shaft controller 300 also executes the mounting control of controlling the second ball screw device 30 such that the dispensing tip 80 is mounted to the tip mounting portion 153A of the head 15 by downward movement of the first frame 21 in the state in which the dispensing tip 80 is not mounted to the head 15.

The first motor 11 is configured to rotate the first threaded shaft 12 to move, in the up-down direction, the piston member 14 integrated with the first nut member 13, thereby sucking and discharging the cell culture solution (the object) by the dispensing tip 80 as described above. The second motor 31 is configured to rotate the second threaded shaft 32 to move, in the Z direction, the first frame 21 equipped with the head 15. The X-axis motor 302 is mounted on an X guide frame (not shown) for guiding movement of the head device 1 in the X direction, and is configured to move the head device 1 in the X direction. The Y-axis motor 301 is mounted on a Y guide frame (not shown) for guiding movement of the head device 1 in the Y direction, and is configured to move the head device 1 in the Y direction.

The shaft controller 300 controls driving of the first motor 11 to control operation of the first nut member 13 in the up-down direction, thereby executing the first control described above. In the suction operation, the shaft controller 300 rotates the first motor 11 forward for a predetermined period of time to lift the piston member 14 by a predetermined distance. In this manner, a predetermined amount of cell culture solution is sucked into the dispensing tip 80. In the discharge operation, the shaft controller 300 rotates the first motor 11 backward for a predetermined period of time to lower the piston member 14 by a predetermined distance. In this manner, the cell culture solution held in the dispensing tip 80 is discharged. A suction speed or a discharge speed is controlled by the rotation speed of the first motor 11.

Moreover, the shaft controller 300 controls driving of the second motor 31 to control the height position of the first frame 21, i.e., the head 15, in the Z direction. By such control, lowering and lifting of the dispensing tip 80 relative to the first container C1 or the second container C2 are performed as described with reference to FIG. 7A and FIG. 7B. In this state, the shaft controller 300 rotates the second motor 31 forward or backward for a predetermined period of time to move the head 15 in the up-down direction within the normal movable area (within the area illustrated in FIG. 8B and FIG. 8C).

Further, the second control and the mounting control as described above are executed by control of the second motor 31 by the shaft controller 300. In the second control, the shaft controller 300 further moves the head 15 upward beyond the upper limit of the normal movable area (see FIG. 8D), and therefore, the dispensing tip 80 is detached from the tip mounting portion 153A. In the mounting control, the shaft controller 300 lowers the head 15 by a movement amount required for fitting the tip mounting portion 153A into the base end portion 81 in the state in which the tip mounting portion 153A of the head 15 and the base end portion 81 of the dispensing tip 80 are aligned to each other in the up-down direction (see FIG. 8A).

In addition to the controls described above, the shaft controller 300 controls driving of the X-axis motor 302 and the Y-axis motor 301 to control movement of the head device 1 in the X direction and the Y direction. In the case where the first container C1 and the second container C2 are present as illustrated in, e.g., FIG. 7A and FIG. 7B, the shaft controller 300 controls the X-axis motor 302 and the Y-axis motor 301 such that the head 15 (the dispensing tip 80) moves from above the first container C1 to above the second container C2. In this manner, the head device 1 is moved.

As described above, according to the head device 1 for mounting the dispensing tip in the present embodiment, the cell culture solution (the liquid containing the object) can be sucked and discharged by the dispensing tip 80 by the movement of the piston member 14 in the up-down direction by driving of the first ball screw device 10 (i.e., the first control). Further, the dispensing tip 80 can be automatically detached from the tip mounting portion 153A of the head 15 by the upward movement of the first frame 21 by driving of the second ball screw device 30 (i.e., the second control). Thus, the process of sucking and discharging the cell culture solution by using the dispensing tip 80 and the process of disposing the used dispensing tip 80 when such a dispensing tip 80 needs to be disposed after use can be highly automated.

Moreover, according to the head device 1, the dispensing tip 80 is detached from the head 15 by the arm member 24 including the guide recess 241 having the opening width (the inner diameter) slightly greater than the outer diameter of the head 15. Thus, the dispensing tip 80 can be detached from the tip mounting portion 153A by simple upward movement of the head 15 relative to the arm member 24.

Further, according to the head device 1, only the replaceable portion 153 of the head 15 to which the dispensing tip 80 is actually mounted can be replaced. Thus, in, e.g., the case where the tip mounting portion 153A is contaminated, the replaceable portion 153 can be detached from the lower end of the rod body 150, and then, can be cleaned. In the case where a dispensing tip 80 having a different opening diameter is mounted to the head 15, it is possible to quickly respond to the change of the opening diameter by attaching another replaceable portion 153 matching such an opening diameter to the rod body 150.

Figure 15:
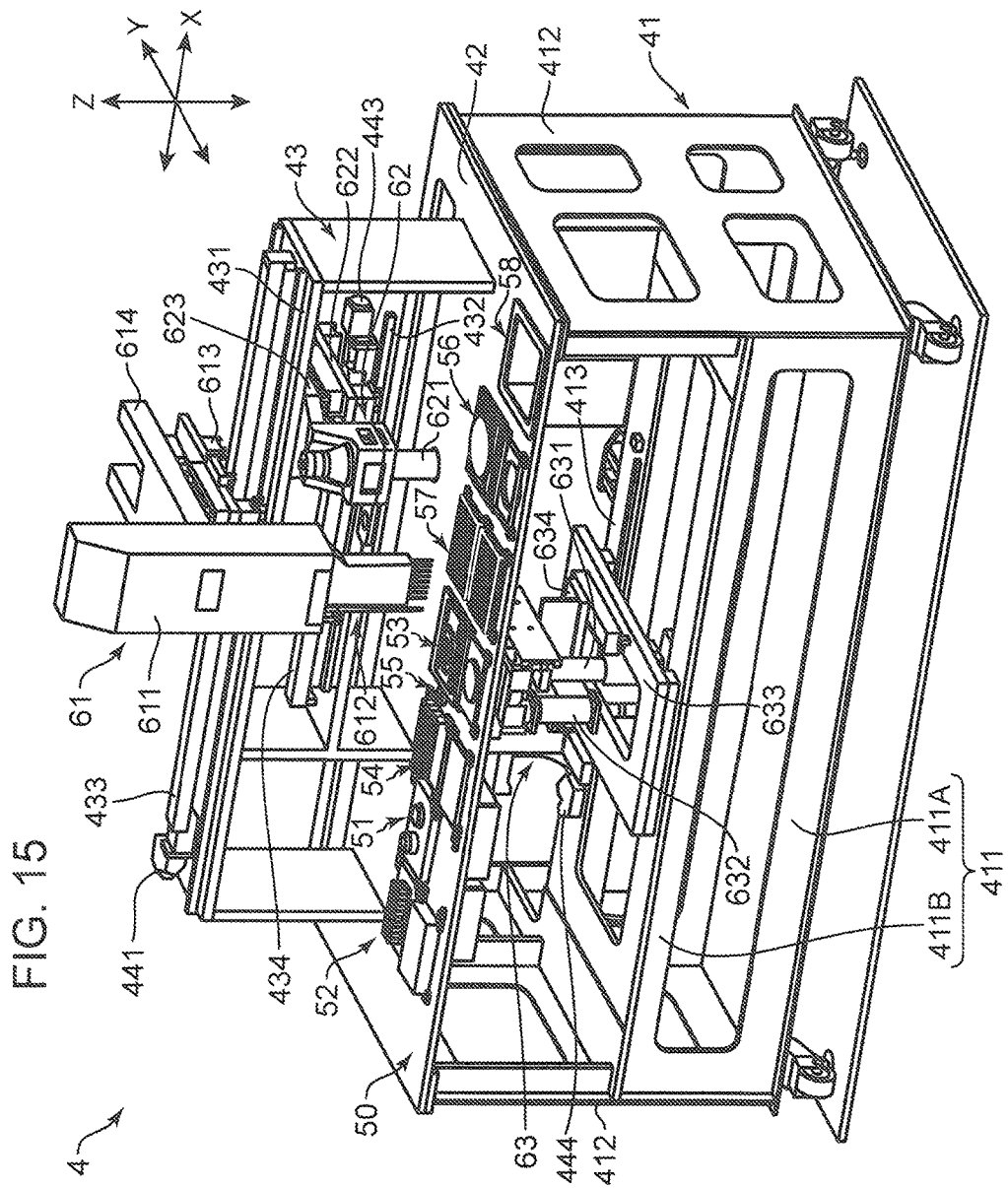
FIG. 15 is a perspective view of a cell movement device to which the head device is applied.
Figure 16:
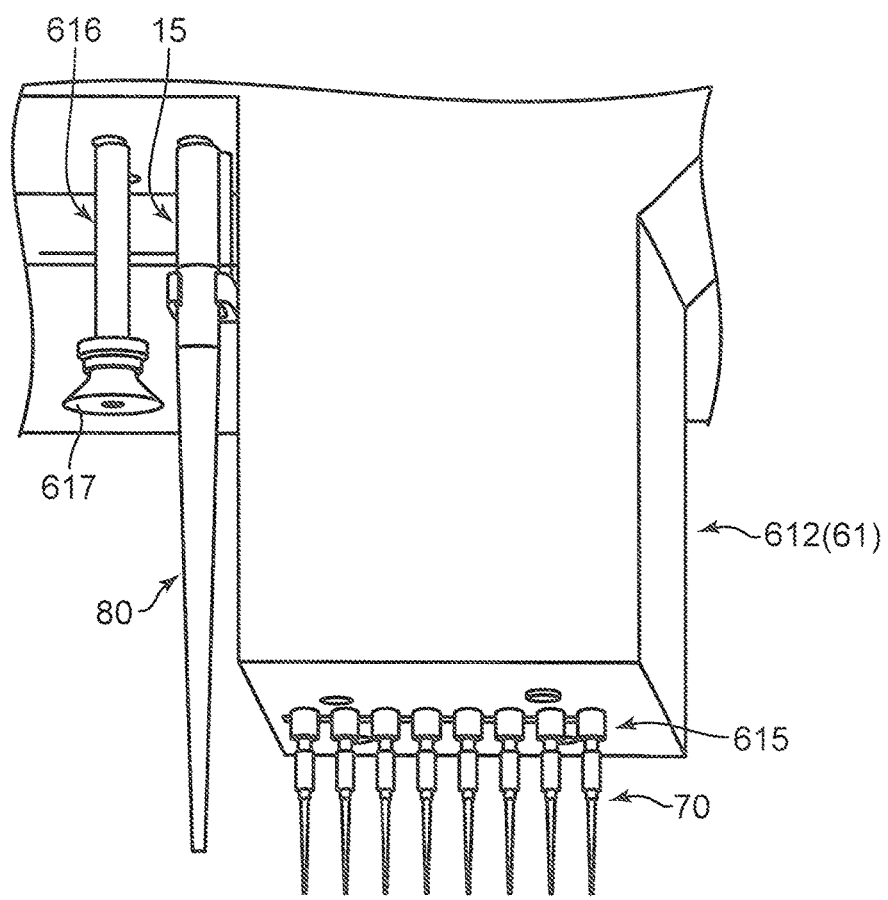
FIG. 16 is a perspective view of a head unit.

Next, a cell movement device 4 to which the head device 1 for mounting the dispensing tip according to the present embodiment is suitably applied will be described as an example. FIG. 15 is a perspective view of the cell movement device 4, and FIG. 16 is a perspective view of a head unit 61 into which the head device 1 is incorporated. The cell movement device 4 includes a support frame 41, a base 42 supported by the support frame 41, a cell movement line 50 assembled with the base 42, the head unit 61 and an illumination unit 62 arranged above the base 42, and an imaging unit 63 disposed below the base 42.

The support frame 41 includes a base frame 411 and a pair of side frames 412. The base frame 411 is a rectangular parallelepiped frame assembly elongated in the X direction. The base frame 411 includes a rectangular lower frame 411A and an upper frame 411B positioned above the lower frame 411A. A guide rail 413 for movement of the imaging unit 63 in the X direction is provided on an upper surface of the upper frame 411B. The base 42 is a rectangular flat plate having predetermined rigidity, partially or entirely made of a translucent material, and having the substantially same size as that of the base frame 411 as viewed from above.

A frame mount 43 stands on the base 42. The frame mount 43 includes upper and intermediate frames 431, 432 as flat plates elongated in the X direction. An upper guide rail 433 for movement of the head unit 61 in the X direction is assembled with an upper surface of the upper frame 431. Moreover, an intermediate guide rail 434 for movement of the illumination unit 62 in the X direction is assembled with an upper surface of the intermediate frame 432.

Elements required for a series of cell movement steps of extracting predetermined cell aggregates from a cell culture solution to move the cell aggregates to a predetermined container are arranged in the X direction on the cell movement line 50. The cell movement line 50 includes an object stocker 51 configured to store a cell culture solution, a dispensing tip stocker 52, a cell sorter 53 configured to sort cell aggregates of the dispensed cell culture solution, a tip stocker 54, a tip imager 55, a cell transferer 56 configured to receive the sorted cell aggregates, a black cover mount 57, and a tip disposer 58. A container included in the object stocker 51 is equivalent to the first container C1 illustrated in FIG. 7A, and a container included in the cell sorter 53 is equivalent to the second container C2 illustrated in FIG. 7B.

The head unit 61 includes a unit body 611, a head portion 612, an X slider 613, and a Y slider 614. As illustrated in FIG. 16, the head portion 612 includes a plurality of cylinder tip heads 615 to which a plurality of cylinder tips 70 are mounted respectively, the head 15 for mounting the dispensing tip 80 as described above, and a nozzle 616. In the present embodiment, an example where eight cylinder tip heads 615 are arranged in line in the X direction is shown. The number of cylinder tip heads 615 may be any number, and the cylinder tip heads 615 may be arranged in a matrix in the XY direction. The nozzle 616 is assembled with the unit body 611 to move up and down, and a lower end of the nozzle 616 is provided with a sucker 617. The mechanisms provided in the first and second ball screw devices 10, 30, etc. as illustrated in FIG. 1 to FIG. 5 and configured to move the head 15 in the Z direction and the mechanism configured to move the cylinder tip heads 615 in the Z direction are built in the unit body 611.

The X slider 613 is assembled with the upper guide rail 433. An X drive motor 441 equivalent to the X-axis motor 302 of FIG. 14 is additionally provided at the upper guide rail 433. Operation of the X drive motor 441 moves the X slider 613 in the X direction on the upper guide rail 433. The Y slider 614 supports the unit body 611 at one end (a front end) in the Y direction. The Y slider 614 is assembled with a Y rail (not shown in FIG. 15) disposed on an upper surface of the X slider 613. A not-shown drive motor (equivalent to the Y-axis motor 301 of FIG. 14) additionally provided at the Y rail operates to move the Y slider 614 and the unit body 611 in the Y direction. That is, the unit body 611 moves along the upper guide rail 433 and the Y rail so that the head portion 612 can freely move in the X direction and the Y direction. Thus, the head portion 612 can move above the base 42 along a predetermined movement path on the cell movement line 50.

The illumination unit 62 is movably disposed above the base 42 to illuminate the cell sorter 53 and the cell transferer 56 from above. Such illumination is used as transillumination when the cell aggregates held by the cell sorter 53 or the cell transferer 56 are imaged by the imaging unit 63. The illumination unit 62 includes an illuminator 621 configured to emit illumination light, an X slider 622, and a holder 623. The X slider 622 is assembled with the intermediate guide rail 434. An illumination unit drive motor 443 is additionally provided at the intermediate guide rail 434. Operation of the drive motor 443 moves the X slider 622 in the X direction on the intermediate guide rail 434. The holder 623 holds the illuminator 621, and is assembled with the X slider 622 to move only a short distance in the Y direction by a not-shown drive device. Thus, the illuminator 621 is movable above the base 42 in the X direction and the Y direction.

The imaging unit 63 is movably disposed below the base 42 to image the cell aggregates held by the cell sorter 53 and the cell transferer 56 from below the base 42. Further, in the present embodiment, the imaging unit 63 is also used to observe the state in which the cylinder tips 70 are mounted to the cylinder tip heads 615 in the tip imager 55. The imaging unit 63 includes a camera 631, an epi-illuminator 632, an X slider 633, and a holder 634.

The camera 631 includes a CCD image sensor and an optical system configured to form an optical image on a light receiving surface of the CCD image sensor. The epi-illuminator 632 is a light source used when an object to be imaged by the camera 631 is not a light transmission body or when the object is subjected to fluorescent staining, for example. The X slider 633 is assembled with the guide rail 413 of the support frame 41. An imaging unit drive motor 444 is additionally provided at the guide rail 413. Operation of the drive motor 444 moves the X slider 633 in the X direction on the guide rail 413. The holder 634 holds the camera 631 and the epi-illuminator 632, and is assembled with the X slider 633 to move only a short distance in the Y direction by a not-shown drive device. Thus, the camera 631 is movable below the base 42 in the X direction and the Y direction.

Figure 17:
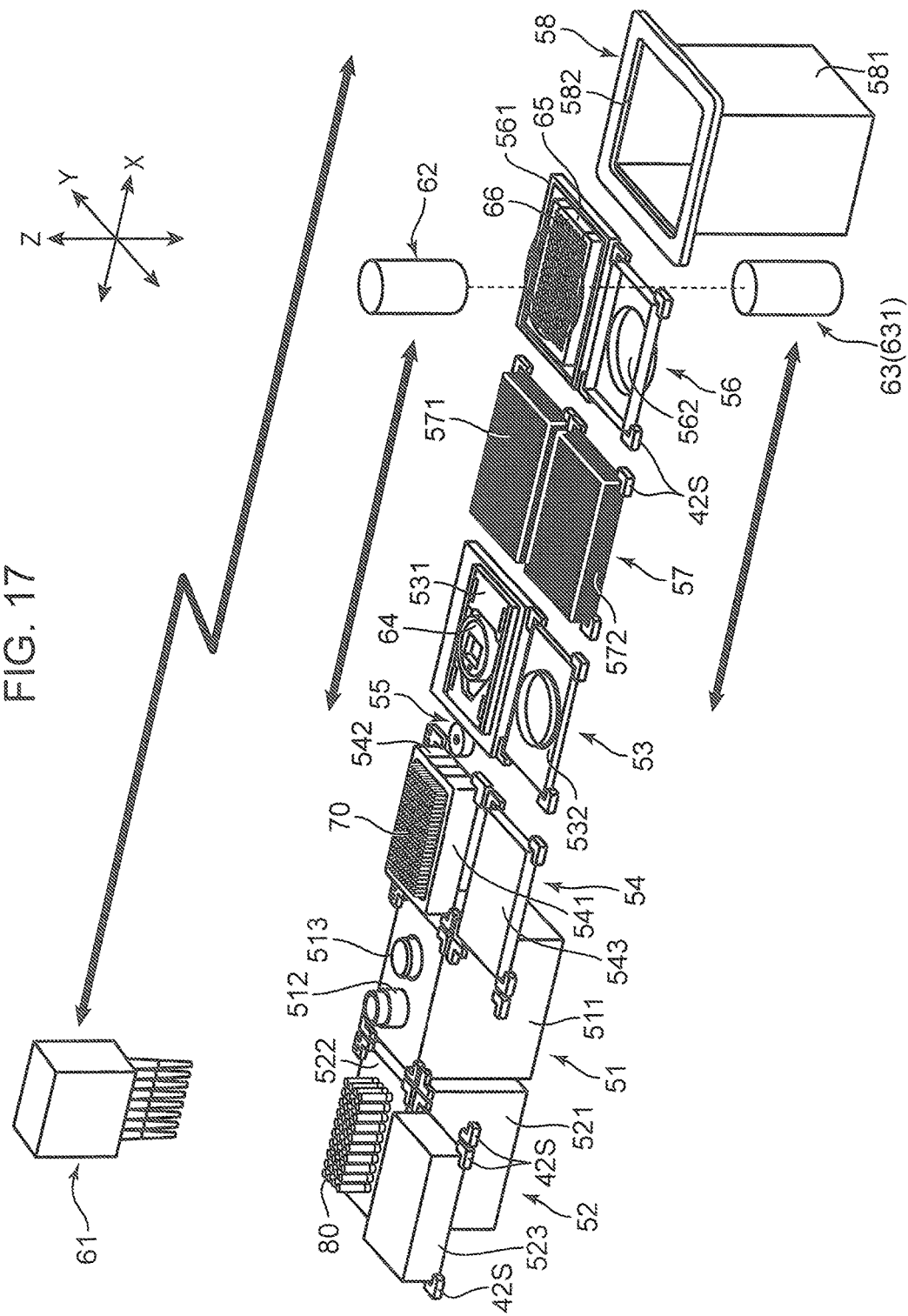
FIG. 17 is a perspective view of components of a cell movement line in the cell movement device.

FIG. 17 is a perspective view of only components of the cell movement line 50 without illustrating the base 42. FIG. 17 also schematically illustrates the arrangement positions of the head unit 61, the illumination unit 62, and the imaging unit 63 described above. The dispensing tip stocker 52, the object stocker 51, the tip stocker 54, the tip imager 55, the cell sorter 53, the black cover mount 57, the cell transferer 56, and the tip disposer 58 are arranged in line in this order from an upstream side (the left end side as viewed in FIG. 17) in the X direction on the cell movement line 50. The position of each of these components on the base 42 is determined by a positioning member 42S. Arrangement on the cell movement line 50 as described herein has been set forth as an example, and the arrangement position of each component can be optionally set considering a working efficiency etc. For example, the black cover mount 57 may be disposed at the front (+Y) or rear (−Y) of the cell sorter 53 and the cell transferer 56.

The object stocker 51 is a component as a dispensing source configured to store a cell culture solution (liquid) containing a large amount of dispersed cell aggregates (an object). The object stocker 51 includes a box 511 disposed at a predetermined position on the base 42, a tube 512 (the first container) held on the box 511, and a lid member 513 mounted on the box 511. The tube 512 is a cylindrical container opening at an upper side thereof, and is configured to store the cell culture solution containing the cell aggregates and impurities. The lid member 513 is a member configured to close the opening of the tube 512.

The dispensing tip stocker 52 is a component configured to store many dispensing tips 80 described above. The dispensing tip stocker 52 includes a holding box 521 configured to hold the dispensing tips 80 aligned in a matrix in a standing state (the state in which each base end portion 81 is positioned above), and a box lid member 523. A holder member 522 configured to align and hold the dispensing tips 80 is disposed in the holding box 521.

The cell sorter 53 is a component configured to sort cell aggregates having a desired size from the cell culture solution containing cell aggregates of various sizes and impurities. The cell sorter 53 includes a dish 64, a holding table 531, and a table lid member 532. The dish 64 is a container opening on an upper side thereof and configured to store the cell culture solution containing the cell aggregates and dispensed by the dispensing tips 80. The holding table 531 is configured to position and hold the dish 64. The table lid member 532 is a lid member configured to cover upper surfaces of the dish 64 and the holding table 531.

The dish 64 includes a well plate having an upper surface provided with a plurality of recesses for supporting the cell aggregates. A through-hole is provided at a bottom portion of each recess. The cell aggregates targeted for extraction are held in the recesses, and the impurities etc. are dropped from the through-holes. Since sorting into the cell aggregates and the impurities is performed as described above, only the cell aggregates remain on the well plate. Images of the cell aggregates supported by the recesses are acquired by the camera 631 under light from the illumination unit 62. Thus, the position of the cell aggregates to be sucked is identified.

The tip stocker 54 is a component configured to hold many cylinder tips 70. Each cylinder tip 70 includes a syringe including, on the inside thereof, a tubular path as a suction path of the cell aggregate, and a plunger slidably contacting an inner peripheral wall of the syringe defining the tubular path while moving back and forth in the tubular path. Each cylinder tip 70 can be mounted/detached to/from the cylinder tip head 615. Each cylinder tip 70 serves the function of sucking the cell aggregate supported in the recess of the well plate described above, delivering the cell aggregate in association with movement of the head unit 61, and discharging the cell aggregate to the cell transferer 56.

The tip stocker 54 includes a holding box 541 and a box lid member 543. The holding box 541 holds the cylinder tips 70 aligned in a matrix in a standing state. A holder member 542 configured to align and hold the cylinder tips 70 is disposed in the holding box 541. Each cylinder tip 70 is held by the holding box 541 such that an upper end portion thereof protrudes upward from an upper end surface of the holding box 541. The box lid member 543 is a lid member placed on the upper end surface of the holding box 541 to cover the cylinder tips 70.

The tip imager 55 is a pit for providing the position where images of the cylinder tips 70 mounted respectively to the cylinder tip heads 615 are acquired. Such imaging is performed by the imaging unit 63. In imaging as described above, the camera 631 of the imaging unit 63 moves to immediately below the tip imager 55, and acquires the image of each cylinder tip 70 under light from the epi-illuminator 632. The XYZ coordinate position of a suction port 71T of each cylinder tip 70 is obtained based on the images of the cylinder tips 70 and focal position information in imaging. A correction value is derived from a difference between the coordinate position and a preset reference position. Such a correction value is utilized as a correction value in movement control of the cylinder tip heads 615. Note that the tip imager 55 itself may be, instead of epi-illuminator 632, equipped with lighting equipment such as an LED light to perform imaging under light from such lighting equipment.

The cell transferer 56 is a component disposed in the vicinity of a downstream end portion of the cell movement line 50 in the X direction and serving as a movement destination of the cell aggregates sucked from the dish 64 of the cell sorter 53. The cell transferer 56 includes a microplate 65, a holding table 561, and a table lid member 562. Note that the cell transferer 56 may be, instead of the microplate 65, equipped with a container similar to the dish 64.

The microplate 65 is a plate configured such that many small wells 66 opening on an upper side thereof are arranged in a matrix. The microplate 65 is formed of a translucent member made of, e.g., transparent plastic. In general, a single cell aggregate is housed in each well 66. Thus, the cell aggregate housed in each well 66 can be imaged by the camera 631. Moreover, the arrangement pitch of the wells 66 is set at the substantially same arrangement pitch as that of the cylinder tips 70 mounted respectively to the cylinder tip heads 615 arranged in line. Thus, the cell aggregates can be discharged at once from the group of the cylinder tips 70 to the wells 66. Note that a selected number of cell aggregates may be housed in each well 66, or a selected amount (the total volume or the total area) of cell aggregates may be housed in each well 66. The holding table 561 is configured to position and hold the microplate 65. The table lid member 562 is a lid member configured to cover upper surfaces of the microplate 65 and the holding table 561.

The black cover mount 57 is a component on which a first black cover 571 covering the cell transferer 56 and a second black cover 572 covering the cell sorter 53 are mounted. The first and second black covers 571, 572 are light shielding bodies used when the cell aggregates supported on the dish 64 or the microplate 65 are imaged in a light shielded state. For example, when a fluorescent agent is added to the cell culture solution for fluorescence observation of the cell aggregates, the first and second black covers 571, 572 cover the holding tables 531, 561, respectively.

The tip disposer 58 is a component disposed at a most downstream end portion of the cell movement line 50 in the X direction so that the used cylinder tips 70 and the used dispensing tips 80 can be disposed after the suction and discharge operations described above. The tip disposer 58 includes a collection box 581 configured to house the used cylinder tips 70 and the used dispensing tips 80. In such a disposition, the head unit 61 equipped with the cylinder tips 70 or the dispensing tips 80 moves to above an opening 582 of the collection box 581, and then, the operation of detaching the cylinder tips 70 from the cylinder tip heads 615 or detaching the dispensing tips 80 from the heads 15 as described above is performed. By such a detachment operation, the cylinder tips 70 or the dispensing tips 80 are dropped into the collection box 581 through the opening 582.

Operation of the movement device 4 configured as described above is controlled by a controller (e.g., a personal computer connected to the movement device 4) equivalent to the shaft controller 300 of FIG. 14. Such a controller causes the movement device 4 to execute operations roughly classified into a dispensing operation using the heads 15 of the present embodiment and a cell movement operation using the cylinder tip heads 615. First, in the dispensing operation, the controller causes the movement device 4 to sequentially execute:
(First Control) the control of moving the head unit 61 to above the dispensing tip stocker 52 and mounting the dispensing tips 80 respectively to the heads 15,
(Second Control) the control of moving the head unit 61 to above the object stocker 51 and causing each dispensing tip 80 to suck a predetermined dispensing amount of a cell culture solution containing cell aggregates and stored in the tube 512,
(Third Control) the control of moving the head unit 61 to above the cell sorter 53 and causing each dispensing tip 80 to discharge the cell culture solution to the dish 64, and
(Fourth Control) the control of moving the head unit 61 to above the tip disposer 58 and detaching the used dispensing tips 80 from the heads 15 to dispose such dispensing tips 80 into the collection box 581.

In the cell movement operation, the controller causes the movement device 4 to sequentially execute:
(Fifth Control) the control of moving the head unit 61 to above the tip stocker 54 and mounting the cylinder tips 70 respectively to the cylinder tip heads 615,
(Sixth Control) the control of moving the head unit 61 to above the cell sorter 53 and causing each cylinder tip 70 to suck the cell aggregate stored in the dish 64,
(Seventh Control) the control of moving the head unit 61 to above the cell transferer 56 and causing each cylinder tip 70 to discharge the cell aggregate to the microplate 65, and
(Eighth Control) the control of moving the head unit 61 to above the tip disposer 58 and detaching the used cylinder tips 70 from the cylinder tip heads 615 to dispose such cylinder tips 70 into the collection box 581.

The first control is the control made for the operation illustrated in FIG. 8A and having been described as the "mounting control" in a description of the shaft controller 300 of FIG. 14. After the head unit 61 has moved to above the dispensing tip stocker 52, each head 15 is aligned to a corresponding one of the dispensing tips 80, and then, is lowered by driving of the second ball screw device 30. By lowering of each head 15, the tip mounting portion 153A is press-fitted into a mounting hole of the base end portion 81 of the dispensing tip 80. Thus, mounting of each dispensing tip 80 to a corresponding one of the heads 15 is completed.

The second and third controls are the controls made for the operation illustrated in FIG. 7A and FIG. 7B and having been described as the "first control" in description of the shaft controller 300. The operation of sucking the cell culture solution into each dispensing tip 80 and the operation of discharging the cell culture solution from each dispensing tip 80 are realized by the first ball screw device 10 and the piston member 14. This point has been described above in detail.

The fourth control is the control made for the operation illustrated in FIG. 8D and having been described as the "second control" in a description of the shaft controller 300. As described above, such a control is for lifting the head 15 beyond the upper limit of the normal movable area by driving of the second ball screw device 30.

According to the movement device 4 described above, the head device 1 of the embodiment of the present disclosure is applied so that a series of processes of mounting each dispensing tip 80 to a corresponding one of the heads 15, sucking the cell culture solution from the tube 512 (the first container C1) by the dispensing tips 80, discharging the cell culture solution to the dish 64 (the second container C2), and disposing the dispensing tips 80 into the tip disposer 58 can be automated under control by the controller described above. Thus, the working efficiency in movement of the cell culture solution containing the cell aggregates can be significantly enhanced.

Note that the specific embodiment described above mainly includes the following configuration aspects.

A head device for mounting a dispensing tip according to an aspect of the present disclosure is a head device to which a dispensing tip configured to suck liquid containing an object and discharge the sucked liquid is mounted. Such a head device includes a piston member, a first shaft member engaging with the piston member to move the piston member in the up-down direction, a tubular rod including a tubular space having a cylinder space in which the piston member is housed to move in the up-down direction and including, at a lower end thereof, a tip mounting portion into which a base end portion of the dispensing tip is fitted, a first frame equipped with the first shaft member and the tubular rod, a second shaft member engaging with the first frame to move the first frame in the up-down direction, a second frame equipped with the second shaft member and including a guide portion configured to guide movement of the tubular rod in the up-down direction in association with the movement of the first frame in the up-down direction, and a shaft controller configured to control operation of the first and second shaft members. The shaft controller executes, in the state in which the dispensing tip is mounted to the tip mounting portion, the first control of controlling the first shaft member such that the dispensing tip sucks and discharges the liquid by the movement of the piston member in the up-down direction, and the second control of controlling the second shaft member such that the guide portion and the base end portion of the dispensing tip come into contact with each other by upward movement of the first frame to detach the dispensing tip from the tip mounting portion.

According to the head device described above, movement of the piston member in the up-down direction by driving of the first shaft member can cause the dispensing tip to suck and discharge the liquid containing the object. Further, upward movement of the first frame by driving of the second shaft member can automatically detach the dispensing tip from the tip mounting portion. Thus, the process of sucking and discharging the object by the dispensing tip and the process of disposing the dispensing tip when such a dispensing tip needs to be disposed after use can be highly automated.

In the head device for mounting the dispensing tip as described above, the tubular rod preferably has a cylindrical shape, the guide portion is preferably an arm member including a guide recess having an inner diameter slightly greater than the outer diameter of the tubular rod, and in the second control, the dispensing tip is preferably detached from the tip mounting portion when a lower end surface of the arm member and an upper edge of the base end portion of the dispensing tip come into contact with each other.

According to such a head device, since the guide recess having an inner diameter slightly greater than the outer diameter of the tubular rod is provided, the dispensing tip can be detached from the tip mounting portion by simple upward movement of the tubular rod relative to the guide member.

In the head device for mounting the dispensing tip as described above, the tubular rod preferably includes a rod body having the cylinder space, and a replaceable portion detachably mounted to a lower end of the rod body, having an interior provided with a tubular space communicating with the cylinder space, and having an outer peripheral surface provided with the tip mounting portion.

According to such a head device, only the portion (the replaceable portion) of the tubular rod to which the dispensing tip is actually mounted can be replaced. Thus, in, e.g., the case where the tip mounting portion is contaminated, the replaceable portion can be detached from the lower end of the rod body, and then, can be cleaned. In the case where a dispensing tip having a different opening diameter is mounted, it is possible to quickly respond to the change of the opening diameter by attaching another replaceable portion matching such an opening diameter to the rod body.

In the head device for mounting the dispensing tip as described above, the first shaft member is preferably a first ball screw device including a first threaded shaft extending in the up-down direction and a first nut member engaging with the first threaded shaft, and the piston member preferably includes an upper end portion provided with an engagement portion fixed to the first nut member, a lower end portion having a peripheral surface provided with a seal member, and an intermediate portion positioned between the upper and lower end portions and having an interior provided with a housing space in which the first threaded shaft is housed.

According to such a head device, a ball screw structure is applied to the first shaft member, and the piston member having a structure adapting to the ball screw structure is employed. Thus, the head device can be configured with a simple structure.

In the head device for mounting the dispensing tip as described above, the second shaft member is preferably a second ball screw device including a second threaded shaft extending in the up-down direction and a second nut member engaging with the second threaded shaft, and the first frame is preferably fixed to the second nut member.

According to such a head device, a ball screw structure can be applied to the second shaft member to move the first frame up and down. Thus, a drive system of the second shaft member can be simplified.

In this case, the second frame preferably includes a longitudinal frame to which a guide rail configured to guide movement of the first frame in the up-down direction is attached, and a transverse frame attached to a lower end of the longitudinal frame, and having a bearing portion for a lower end of the second threaded shaft and a through-hole through which the tubular rod penetrates, the guide portion being assembled with the transverse frame.

According to such a head device, the guide rail and the guide portion can be efficiently arranged using the longitudinal and transverse frames.

A movement device according to another aspect of the present disclosure includes the head device for mounting the dispensing tip as described above, a first container configured to store an object, a second container configured to receive the object, and a head movement mechanism configured to move, in the horizontal direction, the head device between the first and second containers.

According to the present disclosure as described above, suction of the object by the dispensing tip, discharge of the sucked object, and attachment/detachment of the dispensing tip to/from the tubular rod (the head) can be automated. Thus, the working efficiency of moving the object by the dispensing tip can be significantly improved.

The invention claimed is:

1. A head device for mounting a dispensing tip, the head device comprising:
   a mechanism to generate suction force and discharge force;
   a first frame comprising a tubular rod including a tubular space in fluid communication with the mechanism, and including, at a lower end of the tubular rod, a tip mounting portion;
   a first frame movement device to move the first frame in an up-down direction;
   a second frame to guide the movement of the first frame in the up-down direction; and
   a controller to control operation of the mechanism to generate the suction force and the discharge force in the tubular space and the operation of the first frame movement device, by executing
      a first control to control the mechanism to generate the suction force and the discharge force in the tubular space, and
      a second control of controlling the first frame movement device such that the tip mounting portion passes a lower end part of the second frame in the up-down direction by upward movement of the first frame.

2. A movement device comprising:
   the head device according to claim 1;
   a first container to store an object;
   a second container to receive the object; and
   a head movement mechanism to move, in a horizontal direction, the head device between the first and second containers.

3. The head device according to claim 1, wherein
   the mechanism comprises a piston member and a first shaft member engaging with the piston member to move the piston member in the up-down direction, to generate the suction force and the discharge force,
   the first frame comprises the first shaft member,
   the first frame movement device is a second shaft member engaging with the first frame to move the first frame in the up-down direction, and the second frame comprises the second shaft member,
   the controller controls operation of the first and second shaft members, and
   the controller controls the first shaft member such that the the suction force and the discharge force is generated in the tubular space by the movement of the piston member in the up-down direction in the first control, and
   controls the second shaft member to move in the second control.

4. The head device according to claim 3, wherein
   the second frame includes a guide at the end part of the second frame to guide movement of the tubular rod in the up-down direction in accordance with the movement of the first frame in the up-down direction, and
   in the second control, the tip mounting portion passes the guide by the upward movement of the first frame.

5. The head device according to claim 4,
   wherein the tubular rod has a cylindrical shape,
   the guide is an arm member including a guide recess having an inner diameter greater than an outer diameter of the tubular rod, and
   in the second control, the tip mounting portion passes a lower end surface of the arm member.

6. The head device according to claim 4,
   wherein the tubular rod includes
      a rod body having a cylinder space in which the piston member is housed to move in the up-down direction, and
      a replaceable portion detachably mounted to a lower end of the rod body, having an interior provided with a tubular space in fluid communication with the cylinder space, and having an outer peripheral surface provided with the tip mounting portion.

7. The head device according to claim 3, wherein
   the first shaft member is a first ball screw device including a first threaded shaft extending in the up-down direction and a first nut member engaging with the first threaded shaft, and
   the piston member includes
      an upper end portion provided with an engagement portion fixed to the first nut member,
      a lower end portion having a peripheral surface provided with a seal member, and
      an intermediate portion positioned between the upper and lower end portions and having an interior provided with a housing space in which the first threaded shaft is housed.

8. The head device according to claim 3, wherein
   the second shaft member is a second ball screw device including a second threaded shaft extending in the up-down direction and a second nut member engaging with the second threaded shaft, and
   the first frame is fixed to the second nut member.

9. The head device according to claim 8, wherein the second frame includes
   a longitudinal frame to which is attached a guide rail to guide the movement of the first frame in the up-down direction, and
   a transverse frame attached to a lower end of the longitudinal frame, and having a bearing portion for a lower end of the second threaded shaft and a through-hole through which the tubular rod penetrates, with the guide rail coupled with the transverse frame.

* * * * *